(12) United States Patent
Chabrecek et al.

(10) Patent No.: US 6,204,306 B1
(45) Date of Patent: Mar. 20, 2001

(54) FUNCTIONALIZED PHOTOINITIATORS, DERIVATIVES AND MACROMERS THEREFROM AND THEIR USE

(75) Inventors: Peter Chabrecek, Victoria (AU); Kurt Dietliker, Fribourg; Dieter Lohmann, Münchenstein, both of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 08/860,131

(22) PCT Filed: Dec. 18, 1995

(86) PCT No.: PCT/EP95/05012
   § 371 Date: Aug. 11, 1997
   § 102(e) Date: Aug. 11, 1997

(87) PCT Pub. No.: WO96/20919
   PCT Pub. Date: Jul. 11, 1996

(30) Foreign Application Priority Data

Dec. 30, 1994 (CH) .................................... 3968/94

(51) Int. Cl.$^7$ .................................... B29D 11/00
(52) U.S. Cl. .................... 523/106; 523/108; 351/160 R; 351/160 H; 525/243
(58) Field of Search .................... 523/108, 106; 351/160 R, 160 H; 525/243

(56) References Cited

U.S. PATENT DOCUMENTS

| | | | |
|---|---|---|---|
| 4,234,399 | 11/1980 | McDowell et al. | 204/159 |
| 4,582,862 | 4/1986 | Berner et al. | 522/14 |
| 4,977,293 | 12/1990 | Hatton et al. | 558/153 |
| 5,077,402 | 12/1991 | Desobry et al. | 544/87 |
| 5,100,987 | 3/1992 | Hatton et al. | 526/313 |
| 5,527,925 | 6/1996 | Chabrecek et al. | 549/430 |
| 5,532,112 | 7/1996 | Kohler | 430/28.1 |

FOREIGN PATENT DOCUMENTS

| | | |
|---|---|---|
| 0281941 | 9/1988 | (EP) . |
| 0302831 | 2/1989 | (EP) . |
| 0632329 | 1/1995 | (EP) . |
| 1230603 | 1/1989 | (JP) . |
| 6263836 | 9/1994 | (JP) . |

OTHER PUBLICATIONS

Chemical Abstract No. 109:55417r (1988).

*Primary Examiner*—Jeffrey C. Mullis
(74) *Attorney, Agent, or Firm*—R. Scott Meece; Robert J. Gorman, Jr.

(57) ABSTRACT

The present invention relates to α-aminoacetophenones functionalized with organic diisocyanates, which can be used as reactive photoinitiators; to oligomers and polymers to which such functionalized α-aminoacetophenones are bonded; to α-aminoacetophenones having unsaturated polymerizable side-chain; to dimeric and trimeric photoinitiators; to the use of such photoinitiators; to materials coated with such photoinitiators; and to the use of the functionalized α-aminoacetophenones for modifying surfaces.

4 Claims, No Drawings

FUNCTIONALIZED PHOTOINITIATORS, DERIVATIVES AND MACROMERS THEREFROM AND THEIR USE

The present invention relates to α-aminoacetophenones functionalised with organic diisocyanates, which can be used as reactive photoinitiators; to oligomers and polymers to which such functionalised α-aminoacetophenones are bonded; to α-aminoacetophenones having an unsaturated polymerisable side-chain; to dimeric and trimeric photoinitiators; to the use of such photoinitiators; to materials coated with such photoinitiators; and to the use of the functionalised α-aminoacetophenones for modifying surfaces.

Alpha-aminoacetophenones of the structural type (A)

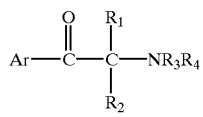

(A)

are known, for example, from EP-A-003 002 and are described therein as outstanding photoinitiators for radiation-induced polymerisation of ethylenically unsaturated monomeric, oligomeric or polymeric compounds. Considered to be a disadvantage are the low-molecular-weight fragments produced which emerge from a polymer, for example as a result of migration, and thus may impair its performance properties. In order to avoid that disadvantage and other disadvantages of such monomeric photoinitiators, EP-A-261 941 proposes modifying photoinitiators at the phenyl nucleus in such a way that the photolysis products are securely bonded into the resulting polymer structure. Also mentioned very generally as functional groups for that purpose are isocyanate groups, which are bonded to the phenyl nucleus via a spacer group, for example a linear alkylene group. The preparation of such compounds poses considerable problems of synthesis, however, since, in the reaction of linear diisocyanates with compounds containing hydroxy groups, the formation of diadducts cannot be avoided or even predominates.

There is therefore a need for functional photoinitiators that can be produced easily, that can be obtained in high purity and are distinguished by high reactivity and stability to storage, that can be linked to suitable oligomers or polymers to produce highly effective macromeric photoinitiators, that are suitable for modifying surfaces, especially plastics surfaces, by photo-induced graft polymerisation, and that can also be used for biologically tolerable materials, especially in the biomedical sector. It has been found that that objective can be achieved by using, for the introduction of isocyanate groups, diisocyanates that comprise isocyanate groups of differing reactivity and reacting them with α-aminoacetophenones that carry in the phenyl nucleus suitable functional groups according to formula (II) to form compounds of formula (I), in which reaction the formation of isomers and other by-products is suppressed by a high regioselectivity.

The invention relates to compounds of formula (I)

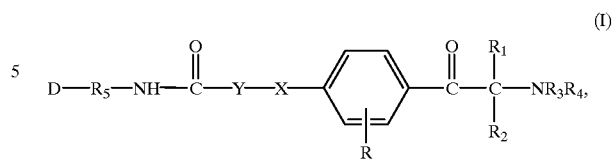

(I)

wherein

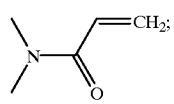

X is bivalent —O—, —NH—, —S—, lower alkylene or

Y is a direct bond or —O—$(CH_2)_n$— wherein n is an integer from 1 to 6 and the terminal $CH_2$ group of which is linked to the adjacent X in formula (I);

R is H, $C_1$–$C_{12}$alkyl, $C_1$–$C_{12}$alkoxy, $C_1$–$C_{12}$alkylNH- or —$NR_{1A}R_{1B}$ wherein $R_{1A}$ is lower alkyl and $R_{1B}$ is H or lower alkyl;

$R_1$ is linear or branched lower alkyl, lower alkenyl or aryl-lower alkyl;

$R_2$ independently of $R_1$ has the same definitions as $R_1$ or is aryl, or $R_1$ and $R_2$ together are —$(CH_2)_m$— wherein m is an integer from 2 to 6;

$R_3$ and $R_4$ are each independently of the other linear or branched lower alkyl that may be substituted by $C_1$–$C_4$alkoxy, or aryl-lower alkyl or lower alkenyl; or $R_3$ and $R_4$ together are —$(CH_2)_z$—$Y_1$—$(CH_2)_z$— wherein $Y_1$ is a direct bond, —O—, —S— or —$NR_{1B}$—, and $R_{1B}$ is H or lower alkyl and z is independently of the other an integer from 2 to 4;

$R_5$ is linear or branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$aralkylene, unsubstituted or $C_1$–$C_4$alkyl- or $C_1$–$C_4$alkoxy-substituted $C_{13}$–$C_{24}$-arylenealkylenearylene, unsubstituted or $C_1$–$C_4$alkyl- or $C_1$–$C_4$alkoxy-substituted $C_3$–$C_8$-cycloalkylene, unsubstituted or $C_1$–$C_4$alkyl- or $C_1$–$C_4$alkoxy-substituted $C_3$–$C_8$cycloalkyl-ene-$C_yH_{2y}$— or unsubstituted or $C_1$–$C_4$alkyl- or $C_1$–$C_4$alkoxy-substituted —$C_yH_{2y}$-($C_3$–$C_8$-cycloalkylene)-$C_yH_{2y}$—, wherein y is an integer from 1 to 6; and D is an isocyanato group.

One preferred definition of X is —O—, —NH— or —S—. Another preferred definition of X is lower alkylene. More preferably, X is —O— or —S— and especially —O—.

In a preferred definition of Y, the index n is 1 to 5, more preferably 2 to 4, and most preferably 2 or 3, so that Y is, for example, ethyleneoxy or propyleneoxy. In another preferred definition, Y is a direct bond, X then preferably containing at least one hetero atom.

The group R contains as alkyl, alkoxy, alkylNH- or —$NR_{1A}R_{1B}$ preferably from 1 to 6 and especially from 1 to 4 carbon atoms. Some examples are methyl, ethyl, n- or iso-propyl, n-, iso- or tert-butyl, pentyl, hexyl, octyl, decyl, dodecyl, methoxy, ethoxy, propoxy, butoxy, N,N- dimethylamino and N-methylamino. Most preferably, R is H. A preferred definition of —NR$_{1A}$R$_{1B}$ is N,N-dimethylamino, N-methylamino, N-methyl-N-ethylamino, N-ethylamino, N,N-diethylamino, N-isopropylamino or N,N-diisopropylamino.

R$_1$ is preferably allyl, benzyl or linear C$_1$–C$_4$alkyl, for example methyl or ethyl.

R$_2$ has preferably the same definitions as R$_1$ and is more preferably linear lower alkyl having from 1 to 4 carbon atoms and especially 1 or 2 carbon atoms. R$_2$ as aryl may be, for example, naphthyl or especially phenyl that is unsubstituted or substituted by lower alkyl or lower alkoxy. When R$_1$ and R$_2$ together are —(CH$_2$)$_m$—, m is preferably 4 or 5 and especially 5.

R$_3$ is preferably linear lower alkyl having from 1 to 4 carbon atoms, benzyl or allyl, and more preferably methyl or ethyl.

R$_4$ is preferably linear lower alkyl having from 1 to 4 carbon atoms and more preferably methyl or ethyl.

When R$_3$ and R$_4$ together are —(CH$_2$)$_z$—Y$_1$—(CH$_2$)$_z$—, Y$_1$ is preferably a direct bond, —O— or —N(CH$_3$)— and most preferably —O—; z is preferably 2 or 3 and especially 2.

R$_5$ is preferably linear or branched C$_3$–C$_{18}$alkylene, unsubstituted or C$_1$–C$_4$alkyl- or C$_1$–C$_4$alkoxy-substituted C$_6$–C$_{10}$arylene, unsubstituted or C$_1$–C$_4$alkyl- or C$_1$–C$_4$alkoxy-substituted C$_{13}$–C$_{24}$arylenealkylenearylene or unsubstituted or C$_1$–C$_4$alkyl- or C$_1$–C$_4$alkoxy-substituted C$_3$–C$_8$cycloalkylene, and preferably linear or branched C$_3$–C$_{11}$alkylene, unsubstituted or C$_1$–C$_2$alkyl- or C$_1$–C$_2$alkoxy-substituted C$_6$–C$_{10}$arylene, unsubstituted or C$_1$–C$_2$-alkyl- or C$_1$–C$_2$alkoxy-substituted C$_{13}$–C$_{24}$arylenealkyleneazylene or unsubstituted or C$_1$–C$_2$alkyl- or C$_1$–C$_2$alkoxy-substituted C$_3$–C$_8$cycloalkylene.

Some examples of linear C$_3$–C$_{18}$alkylene are 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,14-tetradecylene and 1,18-octadecylene.

Some examples of branched C$_3$–C$_{18}$alkylene are 2,2-dimethyl-1,4-butylene, 2,2-dimethyl-1,5-pentylene, 2,2,3- or 2,2,4-trimethyl-1,5-pentylene, 2,2-dimethyl-1,6-hexylene, 2,2,3- or 2,2,4- or 2,2,5-trimethyl-1,6-hexylene, 2,2-dimethyl-1,7-heptylene, 2,2,3- or 2,2,4- or 2,2,5- or 2,2,6-trimethyl-1,7-heptylene, 2,2-dimethyl-1,8-octylene, 2,2,3- or 2,2,4- or 2,2,5- or 2,2,6- or 2,2,7-trimethyl-1,8-octylene.

When R$_5$ is arylene, it is preferably naphthylene and especially phenylene. When the arylene is substituted, one substituent is preferably in the ortho-position with respect to an isocyanate group. Examples of substituted arylene are 1-methyl-2,4-phenylene, 1,5-di-methyl-2,4-phenylene, 1-methoxy-2,4-phenylene and 1-methyl-2,7-naphthylene.

R$_5$ as aralkylene is preferably naphthylalkylene and especially phenylalkylene. The alkylene group in aralkylene contains preferably from 1 to 12, especially from 1 to 6, and more especially from 1 to 4 carbon atoms. Most preferably, the alkylene group in aralkylene is methylene or ethylene. Some examples are 1,3- or 1,4-benzylene, naphth-2-yl-7-methylene, 6-methyl-1,3- or -1,4-benzylene, 6-methoxy-1, 3- or -1,4-benzylene.

When R$_5$ is cycloalkylene, it is preferably C$_5$- or C$_6$-cycloalkylene that is unsubstituted or substituted by methyl. Some examples are 1,3-cyclobutylene, 1,3-cyclopentylene, 1,3- or 1,4-cyclohexylene, 1,3- or 1,4-cycloheptylene, 1,3- or 1,4- or 1,5-cyclooctylene, 4-methyl-1,3-cyclopentylene, 4-methyl-1,3-cyclohexylene, 4,4-dimethyl-1,3-cyclohexylene, 3-methyl- or 3,3-dimethyl-1,4-cyclohexylene, 3,5-dimethyl-1,3-cyclohexylene, 2,4-dimethyl-1,4-cyclohexylene.

When R$_5$ is cycloalkylene-C$_y$H$_{2y}$—, it is preferably cyclopentylene-C$_y$H$_{2y}$— and especially cyclohexylene-C$_y$H$_{2y}$— that is unsubstituted or substituted by preferably from 1 to 3 C$_1$–C$_4$-alkyl groups, especially methyl groups. In the group —C$_y$H$_{2y}$— y is preferably an integer from 1 to 4. More preferably, the group —C$_y$H$_{2y}$— is ethylene and especially methylene.

Some examples are cyclopent-1-yl-3-methylene, 3-methyl-cyclopent-1-yl-3-methylene, 3,4-dimethyl-cyclopent-1-yl-3-methylene, 3,4,4-trimethyl-cyclopent-1-yl-3-methylene, cyclohex-1-yl-3- or -4-methylene, 3- or 4- or 5-methyl-cyclohex-1-yl-3- or -4-methylene, 3,4- or 3,5-dimethyl-cyclohex-1-yl-3- or -4-methylene, 3,4,5- or 3,4,4- or 3,5,5-trimethyl-cyclohex-1-yl-3- or -4-methylene.

When R$_5$ is —C$_y$H$_{2y}$-cycloalkylene-C$_y$H$_{2y}$—, it is preferably —C$_y$H$_{2y}$-cyclopentylene-C$_y$H$_{2y}$- and especially —C$_y$H$_{2y}$-cyclohexylene-C$_y$H$_{2y}$— that is unsubstituted or substituted by preferably from 1 to 3 C$_1$–C$_4$alkyl groups, especially methyl groups. In the group —C$_y$H$_{2y}$—, y is preferably an integer from 1 to 4. More preferably, the groups —C$_y$H$_{2y}$— are ethylene and especially methylene. Some examples are cyclopentane-1,3-dimethylene, 3-methyl-cyclopentane-1,3-dimethylene, 3,4-dimethyl-cyclopentane-1,3-dimethylene, 3,4,4-trimethyl-cyclopentane-1,3-dimethylene, cyclohexane-1,3- or -1,4-dimethylene, 3- or 4- or 5-methyl-cyclohexane-1,3- or -1,4-dimethylene, 3,4- or 3,5-dimethyl-cyclohexane-1,3- or -1,4-dimethylene, or 3,4,5- or 3,4,4- or 3,5,5-trimethyl-cyclohexane-1,3- or -1,4-dimethylene.

A preferred sub-group of compounds of formula I comprises those wherein

R$_1$ is linear lower alkyl, lower alkenyl or aryl-lower alkyl;

R$_2$ independently of R$_1$ has the same definitions as R$_1$ or is aryl;

R$_3$ and R$_4$ are each independently of the other linear or branched lower alkyl that may be substituted by C$_1$–C$_4$alkoxy, or aryl-lower alkyl or lower alkenyl; or R$_3$ and R$_4$ together are —(CH$_2$)$_z$—Y$_1$—(CH$_2$)$_z$— wherein Y1 is a direct bond, —O—, —S— or —NR$_{1B}$—, and R$_{1B}$ is H or lower alkyl and z is an integer from 2 to 4; and R$_5$ is linear or branched C$_3$–C$_{18}$alkylene, unsubstituted or C$_1$–C$_4$alkyl- or C$_1$–C$_4$alkoxy-substituted C$_6$–C$_{10}$arylene, or unsubstituted or C$_1$–C$_4$alkyl- or C$_1$–C$_4$alkoxy-substituted C$_7$–C$_{18}$aralkylene, unsubstituted or C$_1$–C$_4$alkyl- or C$_1$–C$_4$alkoxy-substituted C$_{13}$–C$_{24}$- arylenealkylenearylene, unsubstituted or C$_1$–C$_4$alkyl- or C$_1$–C$_4$alkoxy-substituted C$_3$–C$_8$-cycloalkylene, unsubstituted or C$_1$–C$_4$alkyl- or C$_1$–C$_4$alkoxy-substituted C$_3$–C$_8$cyclo-alkylene-C$_y$H$_{2y}$— or unsubstituted or C$_1$–C$_4$alkyl- or C$_1$–C$_4$alkoxy-substituted -C$_y$H$_{2y}$-(C$_3$–C$_8$cycloalkylene)-C$_y$H$_{2y}$-, wherein y is an integer from 1 to 6.

A preferred sub-group of compounds of formula I comprises those wherein

X is bivalent —O—, —NH—, —S— or —(CH$_2$)$_n$—;

Y is a direct bond or —O—(CH$_2$)$_n$— wherein n is an integer from 1 to 6 and the terminal CH$_2$ group of which is linked to the adjacent X in formula (I);

R is H, C$_1$–C$_{12}$alkyl or C$_1$–C$_{12}$alkoxy;

R$_1$ is linear lower alkyl, lower alkenyl or aryl-lower alkyl;

$R_2$ independently of $R_1$ has the same definitions as $R_1$ or is aryl, or $R_1$ and $R_2$ together are $-(CH_2)_m-$ wherein m is an integer from 2 to 6;

$R_3$ and $R_4$ are each independently of the other linear or branched lower alkyl that may be substituted by $C_1$–$C_4$alkoxy, or aryl-lower alkyl or lower alkenyl; or $R_3$ and $R_4$ together are $-(CH_2)_z-Y_1-(CH_2)_z-$ wherein $Y_1$ is a direct bond, $-O-$, $-S-$ or $-NR_{1B}-$, and $R_{1B}$ is H or lower alkyl and z is an integer from 2 to 4; and $R_5$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-$CH_2$— or cyclohexylene-$CH_2$— substituted by from 1 to 3 methyl groups.

An especially preferred sub-group of compounds of formula I comprises those wherein $R_1$ is methyl, allyl, toluylmethyl or benzyl, $R_2$ is methyl, ethyl, benzyl or phenyl, or $R_1$ and $R_2$ together are pentamethylene, $R_3$ and $R_4$ are each independently of the other lower alkyl having up to 4 carbon atoms, or $R_3$ and $R_4$ together are $-CH_2CH_2OCH_2CH_2-$, and $R_5$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-$CH_2$- or cyclohexylene-$CH_2$- substituted by from 1 to 3 methyl groups.

The group $R_5$ is especially a group in which the reactivity of a OCN group or, possibly, a $NH_2$ or masked $NH_2$ group is reduced, this being achieved essentially by steric hindrance or electronic influences at preferably one of the adjacent carbon atoms. $R_5$ is preferably, therefore, alkylene that is branched in the α-position or especially the β-position with respect to, for example, the OCN group, or is a cyclic hydrocarbon radical that is substituted as defined in at least one α-position.

Some examples of especially preferred compounds are

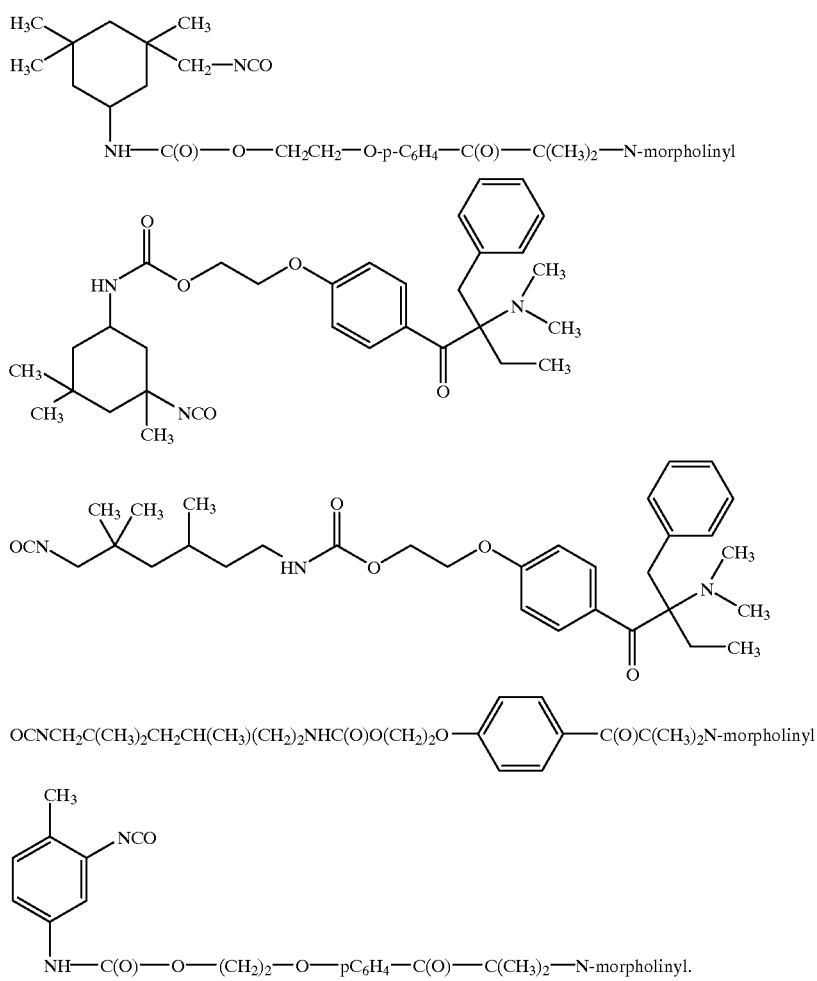

The compounds of formula I can be prepared in a manner known per se by reaction of diisocyanates with the corresponding H-acidic photoinitiators. The compounds are obtained in high yields and purity even when two H-acidic groups, for example two OH groups, of differing reactivity are present in the photoinitiator at the same time. It is especially advantageous to use diisocyanates having isocyanate groups of differing reactivity since the formation of isomers and diadducts can thereby be substantially suppressed. The differing reactivity may be brought about, for example as described hereinabove, by steric hindrance. The differing reactivity may also be achieved by masking one isocyanate group in the diisocyanate, for example as a carboxylic acid or a hydroxylamine.

The invention further relates to a process for the preparation of compounds of formula (I) which comprises reacting a compound of formula II

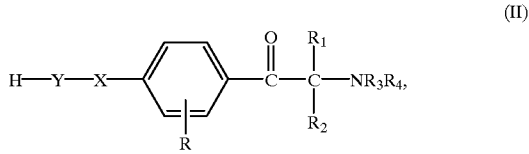

(II)

wherein X, Y, R, $R_1$, $R_2$, $R_3$ and $R_4$ are as defined hereinbefore, preferably in an inert organic solvent, with a diisocyanate of formula III or with such a diisocyanate optionally mono-masked

OCN—$R_5$—NCO   (III), wherein $R_5$ is as defined hereinbefore.

Preferred examples of diisocyanates wherein the reactivity of the two isocyanato groups is distinctly different are e.g. hexane-1,6-diisocyanate, 2,2,4-trimethylhexane-1,6-diisocyanate, 1,3-bis-(3-isocyanatopropyl)-tetramethyldisiloxane, tetramethylenediisocyanate, phenylene-1,4-diisocyanate, toluene-2,4-diisocyanate, toluene-2,6-diisocyanate, m- or p-xylenediisocyanate, isophoronediisocyanate, cyclohexane-1,4-diisocyanate, 1,5-naphthylenediisocyanate, 4,4'-diphenylmethanediisocyanate, 4,4'-diphenylsulfonediisocyanate or 4,4'-dicyclohexylmethanediisocyanate.

Masking agents are known from urethane chemistry. They may be, for example, phenols (cresol, xylenol), lactams (ε-caprolactam), oximes (acetoxime, benzophenone oxime), H-active methylene compounds (diethyl malonate, ethyl acetoacetate), pyrazoles or benzotriazoles. Masking agents are described, for example, by Z. W. Wicks, Jr. in Progress in Organic Coatings, 9 (1981), pages 3–28.

The starting materials of the type shown in formula II are known and are described, for example, in EP-A-284 561, EP-A-1 17 233 or EP-A-088 050.

Suitable inert solvents are aprotic, preferably polar, solvents such as, for example, hydrocarbons (petroleum ether, methylcyclohexane, benzene, toluene, xylene), halogenated hydrocarbons (chloroform, methylene chloride, trichloroethane, tetrachloroethane, chlorobenzene), ethers (diethyl ether, dibutyl ether, ethylene glycol dimethyl ether, diethylene glycol dimethyl ether, tetrahydrofuran (THF), dioxane), ketones (acetone, dibutyl ketone, methyl isobutyl ketone), carboxylic acid esters and lactones (ethyl acetate, butyrolactone, valerolactone), alkylated carboxylic acid amides (N,N-dimethylacetamide (DMA) or N,N-dimethylformamide (DMF), N-methyl-2-pyrrolidone (NMP)), nitriles (acetonitrile), sulfones and sulfoxides (dimethyl sulfoxide (DMSO), tetramethylenesulfone). Polar solvents are preferably used.

The reactants are advantageously used in equimolar quantities. The reaction temperature may, for example, be from 0 to 200° C. When using catalysts, the temperatures may advantageously be in the range from −20° to 60° C. and preferably in the range from −10° to 50° C. Suitable catalysts are, for example, metal salts, such as alkali metal salts, of carboxylic acids, tertiary amines, for example tri-lower alkyl amines (triethylamine, tri-n-butyl-amine), N-methylpyrrolidine, N-methylmorpholine, N,N-dimethylpiperidine, pyridine and 1,4-iaza-bicyclooctane. Tin compounds have been found to be especially effective, especially alkyltin salts of carboxylic acids, such as, for example, dibutyltin dilaurate, or, for example, tin dioctoate.

If free NH groups are present in the compounds of formula I, those groups can initially be protected by suitable protecting groups during the reaction with a diisocyanate and subsequently freed again by removing the protecting groups. Suitable protecting groups are known to the person skilled in the art. Representative examples can be found, for example, in T. W. Greene, "Protective Groups in Organic Synthesis", Wiley Interscience, 1981.

The isolation and purification of the compounds prepared are carried out in accordance with known methods, for example extraction, crystallisation, re-crystallisation or chromatographic purification methods. The compounds are obtained in high yields and purity. The yields in the case of non-optimised processes may be more than 85% of the theoretical yields.

The compounds of formula (I) are outstandingly suitable as photoinitiators for ethylenically unsaturated radically polymerisable compounds. In that case, the oligomers and polymers so produced carry one, two or more terminal isocyanate groups. The invention further relates to the use of a compound according to formula (I) as a photoinitiator for ethylenically unsaturated radically polymerisable compounds.

The compounds according to formula (I) are also outstandingly suitable for the preparation of oligomeric and polymeric photoinitiators by reaction with functional oligomers or polymers that contain active H atoms in terminal or pendant groups, for example OH or NH groups. These macromeric photoinitiators are distinguished by good tolerability and high effectiveness, the photochemical decomposition products being covalently bonded into the resulting polymers, for example as chain initiators or terminators, so that a long service life is ensured. A further advantage to be mentioned is the special structure of the photopolymers, since the polymer chains grow on the macromeric photoinitiator as terminal or pendant blocks, as a result of which additional advantageous performance properties are produced. By the choice of oligomers or polymers, therefore, it is possible to establish desired properties in the photopolymer in a controlled manner.

The invention further relates to oligomers or polymers having H-active groups —OH and/or —NH— bonded to the oligomer or polymer backbone terminally (1 or 2 groups) or pendantly (one or more groups), if desired via a bridge group, or having H-active —NH— groups bonded in the oligomer or polymer backbone, the H atoms of which H-active groups are partly or completely substituted by radicals of formula IV

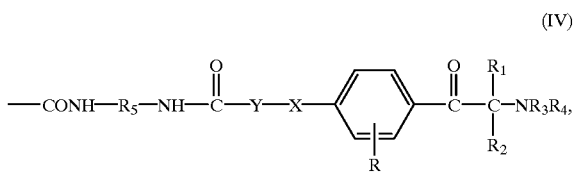

(IV)

wherein R, $R_1$, $R_2$, $R_3$, $R_4$, $R_5$, X and Y are as defined hereinbefore.

The H-active groups are preferably —COOH, OH— or —NH— groups.

The oligomers may have, for example, an average molecular weight of from 300 to 10000 dalton and contain preferably at least 3, more preferably from 3 to 50 and especially from 5 to 20 structural units. As is known, the transition between oligomers and polymers is fluid and cannot be defined exactly. The polymers may contain from 50 to 10000, more preferably from 50 to 5000, structural units and may have an average molecular weight of from 10000 to 1000000, preferably from 10000 to 500000. The oligomers and polymers may also comprise up to 95 mol %, preferably from 5 to 90 mol %, comonomeric structural units without H-active groups, based on the polymer.

The oligomers and polymers having H-active groups may be natural or synthetic oligomers or polymers.

Natural oligomers and polymers are, for example, oligo- and poly-saccharides or derivatives thereof, proteins, glycoproteins, enzymes and growth factors. Some examples are cyclodextrins, starch, hyaluronic acid, deacetylated hyaluronic acid, chitosan, trehalose, cellobiose, maltotriose, maltohexaose, chitohexaose, agarose, chitin 50, amylose, glucanes, heparin, xylan, pectin, galactan, polygalactosamine, glycosaminoglycanes, dextran, aminated dextran, cellulose, hydroxyalkylcelluloses, carboxyalkylcelluloses, fucoidan, chondroitin sulfate, sulfated polysaccharides, mucopolysaccharides, gelatin, zein, collagen, albumin, globulin, bilirubin, ovalbumin, keratin, fibronectin and vitronectin, pepsin, trypsin and lysozyme.

The synthetic oligomers and polymers may be substances containing the groups —COOH, —OH, —NH$_2$ or —NHR$_6$, wherein R$_6$ is C$_1$–C$_6$alkyl. They may be, for example, hydrolysed polymers of vinyl esters or ethers (polyvinyl alcohol); hydroxylated polydiolefins, e.g. polybutadiene, polyisoprene or polychloroprene; polyacrylic acid and polymethacrylic acid and also polyacrylates, polymethacrylates, polyacrylamides or polymethacrylamides having hydroxyalkyl or aminoalkyl radicals in the ester group or amide group; polysiloxanes having hydroxyalkyl or aminoalkyl groups; polyethers of epoxides or glycidyl compounds and diols; polyvinylphenols or copolymers of vinylphenol and olefinic comonomers; and copolymers of at least one monomer from the group vinyl alcohol, vinylpyrrolidone, acrylic acid, methacrylic acid, or hydroxyalkyl- or aminoalkyl-containing acrylates, methacrylates, or acrylamide or methacrylamide, or hydroxylated diolefins with ethylenically unsaturated comonomers, e.g. acrylonitrile, olefins, diolefins, vinyl chloride, vinylidene chloride, vinyl fluoride, vinylidene fluoride, styrene, α-methylstyrene, vinyl ethers and vinyl esters; or polyoxaalkylenes having terminal OH or aminoalkyloxy groups.

Preferred oligomers and polymers are, for example, cyclodextrins having a total of from 6 to 8 glucose structural units forming a ring, or hydroxyalkyl or aminoalkyl derivatives or glucose- or maltose-substituted derivatives, of which at least one structural unit corresponds to formula (V)

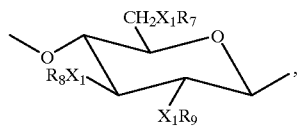

(V)

wherein

R$_7$, R$_8$ and R$_9$ are each independently of the others H, C$_1$–C$_4$alkyl, especially methyl, C$_2$–C$_6$acyl, especially acetyl, C$_1$–C$_4$hydroxyalkyl, especially hydroxymethyl or 2-hydroxyeth-1-yl, C$_2$–C$_{10}$aminoalkyl and especially C$_2$–C$_4$aminoalkyl, for example 2-aminoeth-1-yl or 3-aminoprop-1-yl or 4-aminobut-1-yl, X$_1$ is —O— or —NR$_{1B}$—, wherein, per cyclodextrin unit, a total of from 1 to 10 and preferably from 1 to 6 radicals X$_1$ may be —NR$_{1B}$— and the remaining radicals X$_1$ are —O—, wherein R$_{1B}$ is hydrogen or lower alkyl; and at least one of the radicals R$_7$, R$_8$ and R$_9$ is a radical of formula (VI)

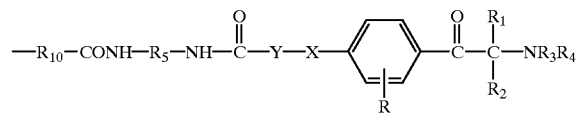

(VI)

wherein

R, R$_1$, R$_2$, R$_3$, R$_4$, R$_5$, X and Y are as defined hereinbefore, and

R$_{10}$ is a direct bond, -(C$_1$–C$_6$alkylene-O)- or -(C$_2$–C$_{10}$alkylene-NH)-, wherein the hetero atom is linked to the carbonyl in formula (VI).

In a preferred embodiment, from at least half the glucose units to all 6 to 8 of the glucose units contain at least one radical of formula (VI). Also preferred is an embodiment in which only one glucose unit carries a radical of formula (VI). For R, R$_1$, R$_2$, R$_3$, R4, R$_5$, X and Y the preferred definitions given above apply. R$_{10}$ is preferably a direct bond, —CH$_2$—O—, —CH$_2$CH$_2$—O—, —CH$_2$CH$_2$—NH— or —CH$_2$CH$_2$CH$_2$—NH—.

Other preferred oligomers and polymers are, for example, oligo- and poly-siloxanes having OH or NH$_2$ groups in alkyl, alkoxyalkyl or aminoalkyl terminal groups or side-chains, the H atoms of which are substituted by a photoinitiator according to the invention. They may be random or block oligomers or random or block polymers. More preferred are those oligomers and polymers which comprise a) from 5 to 100 mol % structural units of formula (VII)

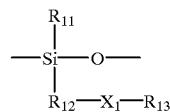

(VII)

and b) from 95 to 0 mol % structural units of formula (VIII)

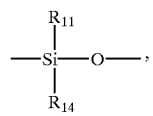

(VIII)

based on the oligomer or polymer, wherein

R$_{11}$ is C$_1$–C$_4$alkyl, lower alkenyl, cyano-lower alkyl or aryl each unsubstituted or partly or completely substituted by F, and is preferably methyl, ethyl, vinyl, allyl, cyanopropyl or trifluoromethyl, R$_{12}$ is C$_2$–C$_6$alkylene, preferably 1,3-propylene, —(CH$_2$)$_z$—(O—CH$_2$—CHCH$_3$—)$_z$—, —(CH$_2$)$_z$—

—(O—CH$_2$—CH$_2$)$_z$— or —(CH$_2$)$_z$—NH—(CH$_2$)$_z$—NH—, preferably —(CH$_2$)$_3$—(O—CH$_2$—CHCH$_3$—)$_2$— or —(CH$_2$)$_3$—NH—(CH$_2$)$_2$—NH—, wherein z is independently of the other an integer from 2 to 4, $R_{14}$ has the same definitions as $R_{11}$ or is —$R_{12}$—$X_1$—H or —$R_{12}$—$X_1$—$R_{15}$—H, $X_1$ is —O— or —NH—, and $R_{13}$ is a radical of formula (IX)

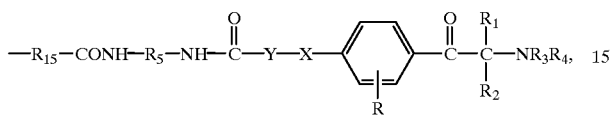

(IX)

wherein

R, $R_1$, $R_2$, $R_3$, $R_4$, $R_5$, X and Y are as defined hereinbefore, and $R_{15}$ is a direct bond or a group —C(O)—(CHOH)$_r$—CH$_2$—O— wherein r is 0 or an integer from 1 to 4.

For R, $R_1$, $R_2$, $R_3$, $R_4$, $R_5$, X and Y the preferred definitions given above apply. $X_1$ is preferably —NH—.

Preferred oligomeric and polymeric siloxanes are also those of formula (X)

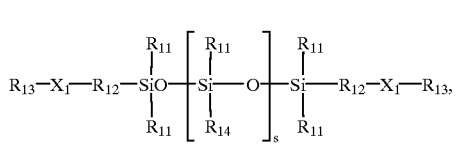

(X)

wherein $R_{11}$ is C$_1$–C$_4$alkyl, vinyl, allyl or phenyl each unsubstituted or partly or completely substituted by F, and is preferably methyl, $R_{12}$ is C$_2$–C$_6$alkylene, preferably 1,3-propylene, $R_{14}$ has the same definitions as $R_{11}$ or is —$R_{12}$—$X_1$—H or —$R_{12}$—$X_1$—$R_{15}$—H, $X_1$ is —O— or —NH—, s is an integer from 1 to 1000 and preferably from 1 to 100, and $R_{13}$ is a radical of the above formula (IX) wherein R, $R_1$, $R_2$, $R_3$, $R_4$, $R_5$, X and Y are as defined hereinbefore, and $R_{15}$ is a direct bond or a group —C(O)—(CHOH)$_r$—CH$_2$—O— wherein r is 0 or an integer from 1 to 4.

For R, $R_1$, $R_2$, $R_3$, $R_4$, $R_5$, X and Y the preferred definitions given above apply. $X_1$ is preferably —NH—.

Other preferred oligomers and polymers are those based on oligovinyl and polyvinyl alcohol in which the H atoms in the OH groups are partly or completely substituted by a radical of formula (VI). They may be homopolymers with —CH$_2$CH(OH)— structural units or copolymers with other monovalent or bivalent structural units of olefins.

More preferred are those oligomers and polymers which comprise a) from 5 to 100 mol % structural units of formula (XI)

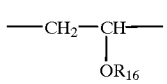

(XI)

and b) from 95 to 0 mol % structural units of formula (XII)

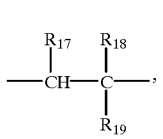

(XII)

wherein $R_{16}$ is a radical of the above formula (VI) wherein R, $R_1$, $R_2$, $R_3$, $R_4$, $R_5$, X and Y are as defined hereinbefore and $R_{10}$ is a direct bond, -(C$_1$–C$_4$alkylene-O)- or -(C$_2$–C$_{10}$-alkylene-NH)-;

$R_{17}$ is H, C$_1$–C$_6$alkyl, —COOR$_{20}$ or —COO$^\ominus$, $R_{18}$ is H, F, Cl, CN or C$_1$–C$_6$alkyl, and $R_{19}$ is H, OH, $R_{10}$—H, F, Cl, CN, $R_{20}$—O—, C$_1$–C$_{12}$alkyl, —COO$^\ominus$, —COOR$_{20}$, —OCO—R$_{20}$, methylphenyl or phenyl, wherein $R_{20}$ is C$_1$–C$_{18}$alkyl, C$_5$–C$_7$cycloalkyl, (C$_1$–C$_{12}$alkyl)-C$_5$–C$_7$cycloalkyl, phenyl, (C$_1$–C$_{12}$alkyl)phenyl, benzyl or (C$_1$–C$_{12}$alkyl)benzyl.

$R_{17}$ is preferably H. When $R_{17}$ is alkyl, it is preferably methyl or ethyl. When $R_{17}$ is —COOR$_{20}$, $R_{20}$ is preferably C$_1$–C$_{12}$alkyl, especially C$_1$–C$_6$alkyl.

When $R_{18}$ is alkyl, it is preferably C$_1$–C$_4$alkyl, e.g. methyl, ethyl, n-propyl or n-butyl. $R_{18}$ is preferably H, Cl or C$_1$–C$_4$alkyl.

When $R_{19}$ is the group $R_{20}$—O—, $R_{20}$ is preferably C$_1$–C$_{12}$alkyl, especially C$_1$–C$_6$alkyl. When $R_{19}$ is alkyl, it preferably contains from 1 to 6, especially from 1 to 4, carbon atoms. When $R_{19}$ is the group —COOR$_{20}$, $R_{20}$ is preferably C$_1$–C$_{12}$alkyl, especially C$_1$–C$_6$alkyl, or cyclopentyl or cyclohexyl. When $R_{19}$ is the group —OCO—R$_{20}$, $R_{20}$ is preferably C$_1$–C$_{12}$alkyl, especially C$_1$–C$_6$alkyl, or phenyl or benzyl.

In a preferred embodiment, $R_{17}$ is H, $R_{18}$ is H, F, Cl, methyl or ethyl, and $R_{19}$ is H, OH, F, Cl, CN, C$_1$–C$_4$alkyl, C$_1$–C$_6$alkoxy, C$_1$–C$_6$hydroxyalkoxy, —COO-C$_1$–C$_6$alkyl, —OOC-C$_1$–C$_6$alkyl or phenyl.

Especially preferred are those oligomers and polymers wherein $R_{17}$ is H, $R_{18}$ is H or methyl, and $R_{19}$ is H, OH, CN, methyl, OCH$_3$, O(CH$_2$)$_t$OH or —COOCH$_3$, and t is an integer from 2 to 6.

Another preferred group of oligomers and polymers comprises partially or completely hydroxyalkylated oligo- or poly-acrylates or -methacrylates, or -acrylamides or -methacrylamides, in which the primary hydroxy group or amino group, respectively, is substituted by a radical of the above formula (IX). They may comprise, for example, from 5 to 100 mol % structural units of formula (XII)

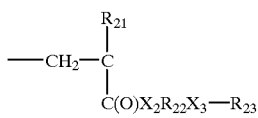

(XIII)

and from 95 to 0 mol % structural units of formula (XIV)

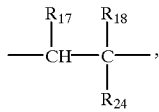

(XIV)

wherein $R_{21}$ is H or methyl, $X_2$ and $X_3$ are each independently of the other —O— or —NH—, $R_{22}$ is —$(CH_2)_c$— and c is an integer from 2 to 12, preferably from 2 to 6, $R_{23}$ is a radical of formula (IX), $R_{17}$ and $R_{18}$ are as defined hereinbefore, and $R_{24}$ has the same definitions as $R_{19}$ or is —C(O)$X_2R_{22}X_3$H.

For $R_{23}$, $R_{17}$, $R_{18}$ and $R_{19}$ the preferred definitions mentioned hereinbefore apply. For $X_2$ and $X_3$ the preferred definitions mentioned hereinbefore apply.

Other preferred oligomers and polymers are those consisting of polyalkylene oxides in which the H atoms of the terminal OH or —$NH_2$ groups are partly or completely substituted by radicals of formula (IX). They may, for example, be those of formula (XV) having identical or different structural repeating units —[$CH_2CH(R_{26})$—O]—

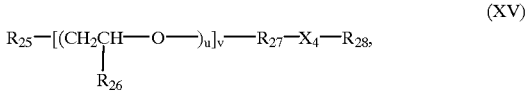

(XV)

wherein $R_{25}$ is the group $R_{28}$—$X_4$— or is the v-valent radical of an alcohol or polyol having from 1 to 20 carbon atoms, $R_{26}$ is H, $C_1$–$C_8$alkyl, preferably $C_1$–$C_4$alkyl and especially methyl, $R_{27}$ together with $X_4$ is a direct bond or $R_{27}$ is $C_2$–$C_6$alkylene, preferably $C_3$–$C_6$alkylene and especially 1,3-propylene, $X_4$ is —O— or —NH—, $R_{28}$ is a radical of formula (IX), u is independently of the other a numerical value from 3 to 10000, preferably from 5 to 5000, especially from 5 to 1000 and more especially from 5 to 100, and v is an integer from 1 to 6, preferably from 1 to 4.

$R_{25}$ may be a mono- to tetra-valent radical of an alcohol or polyol. When $R_{25}$ is the radical of an alcohol, $R_{25}$ is preferably linear or branched $C_3$–$C_{20}$-alkyl or -alkenyl, $C_3$–$C_8$- and especially $C_5$–$C_6$-cycloalkyl, —$CH_2$-($C_5$–$C_6$cycloalkyl), $C_6$–$C_{10}$aryl and especially phenyl and naphthyl, $C_7$–$C_{16}$aralkyl and especially benzyl and 1-phenyleth-2-yl. The cyclic or aromatic radicals may be substituted by $C_1$–$C_{18}$alkyl or $C_1$–$C_{18}$alkoxy.

When $R_{25}$ is the radical of a diol, $R_{25}$ is preferably branched and especially linear $C_3$–$C_{20}$-alkylene or alk-enylene and more preferably $C_3$–$C_{12}$alkylene, $C_3$–$C_8$- and especially $C_5$–$C_6$-cycloalkylene, —$CH_2$-($C_5$–$C_6$cycloalkyl)-, —$CH_2$-($C_5$–$C_6$cycloalkyl)-$CH_2$—, $C_7$–$C_{16}$aralkylene and especially benzylene, —$CH_2$-($C_6$–$C_{10}$aryl)-$CH_2$— and especially xylylene. The cyclic or aromatic radicals may be substituted by $C_1$–$C_{12}$alkyl or $C_1$–$C_{12}$alkoxy.

When $R_{25}$ is a trivalent radical, it is derived from aliphatic or aromatic triols. $R_{25}$ is preferably a trivalent aliphatic radical having from 3 to 12 carbon atoms that is derived especially from triols having preferably primary hydroxy groups. Most preferably, $R_{25}$ is —$CH_2$(CH—)$CH_2$—, HC($CH_2$—)$_3$ or $CH_3C(CH_2$—)$_3$.

When $R_{25}$ is a tetravalent radical, it is derived preferably from aliphatic tetrols. $R_{25}$ is in that case preferably C($CH_2$—)$_4$.

Preferably, $R_{25}$ is a radical derived from Jeffamins (Texaco), a Pluriol, a Poloxamer (BASF) or poly(tetmnethylene oxide).

For $R_{28}$ the preferred definitions mentioned hereinbefore apply. Especially preferred are homo-oligomers and homo-polymers and block oligomers and block polymers each having structural units of the formula —[$CH_2CH_2$—O]— or —[$CH_2CH(CH_3)$—O]—.

Also suitable are fluorinated polyethers corresponding to formula (XVI)

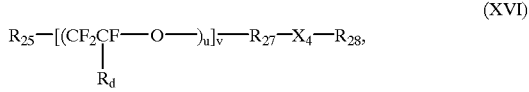

(XVI)

wherein $R_{27}$, $R_{28}$, $X_4$, u and v are as defined hereinbefore, $R_{25}$ is as defined hereinbefore or is the monovalent radical of a partly fluorinated or per-fluorinated alcohol having from 1 to 20, preferably from 1 to 12 and especially from 1 to 6 carbon atoms, or the bivalent radical of a partly fluorinated or per-fluorinated diol having from 2 to 6, preferably from 2 to 4 and especially 2 or 3 carbon atoms, and $R_d$ is F or perfluoroalkyl having from 1 to 12, preferably from 1 to 6 and especially from 1 to 4 carbon atoms.

$R_d$ is especially —$CF_3$.

Other suitable oligomers and polymers are, for example, polyamines, for example polyvinylamine, or polyethyleneimines, in which the H atoms of the NH groups are substituted by a radical of formula (VI), including the preferences already mentioned. Also suitable is poly-ε-lysine.

The oligomers and polymers according to the invention can be prepared simply and in a manner known per se by reaction of a compound of formula (I) with HO— or NH-functional oligomers and polymers.

The photoinitiators of formula (I) according to the invention can also be used for the preparation of polymerisable photoinitiators having ethylenically unsaturated groups by reacting a compound of formula (I) with OH— or NH-functional ethylenically unsaturated compounds. That reaction is known to one skilled in the art and will not be described in more detail. OH- and NH-functional ethylenically unsaturated compounds are, for example, (hydroxyalkyl)- or (aminoalkyl)-acrylic or -methacrylic acid esters or amides.

The invention further relates to compounds of formula (XVII)

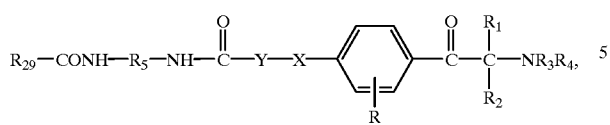

(XVII)

wherein

X, Y, R, $R_1$, $R_2$, $R_3$, $R_4$ and $R_5$ have the definitions given hereinbefore, including the preferred definitions, and $R_{29}$ is a vinylic, radically polymerisable hydrocarbon having from 2 to 12 carbon atoms or is a radical of formula (XVIII)

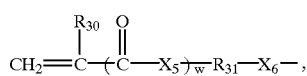

(XVIII)

wherein $R_{30}$ is H or methyl, $R_{31}$ is branched or, preferably, linear $C_1$–$C_{12}$alkylene, lower alkylenearylene or arylene- lower alkylene, or, when w=0, $R_{31}$ may be a bond, w is zero or 1 and $X_5$ and $X_6$ are each independently of the other —O— or —NH—.

$R_{31}$ is preferably $C_2$–$C_6$alkylene, for example ethylene, 1,3-propylene, 1,4-butylene, 1,5-pentylene and 1,6-hexylene.

When $R_{29}$ is a vinylic, radically polymerisable hydrocarbon, it is, for example, alkenyl, vinylphenyl or vinylbenzyl as a radically polymerisable group having preferably from 2 to 12 carbon atoms. Examples of alkenyl are vinyl, allyl, 1-propen-2-yl, 1-buten-2- or -3- or -4-yl, 2-buten-3-yl, and the isomers of pentenyl, hexenyl, octenyl, decenyl, undecenyl and dodecenyl. $R_{29}$ contains preferably from 2 to 12, especially from 2 to 8, carbon atoms. In a preferred definition, within the scope of this invention $R_{29}$ is alkenyl having from 2 to 4 carbon atoms.

Some examples are:

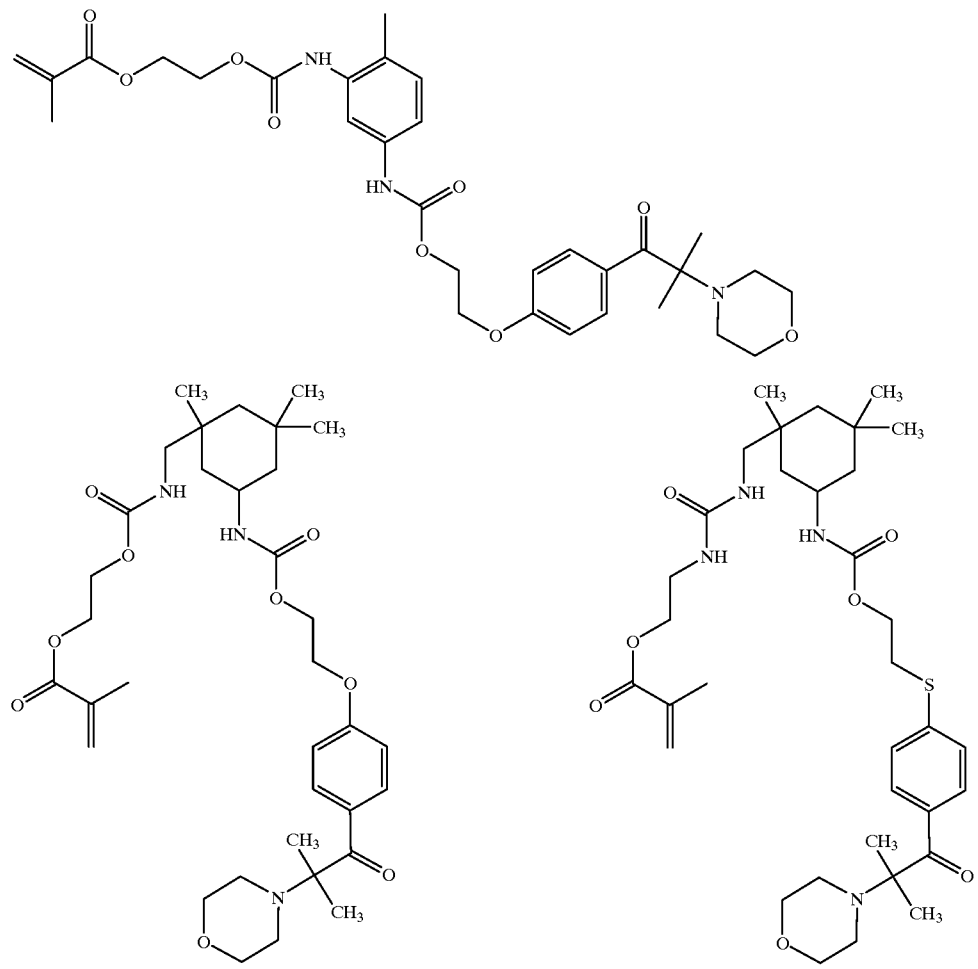

-continued

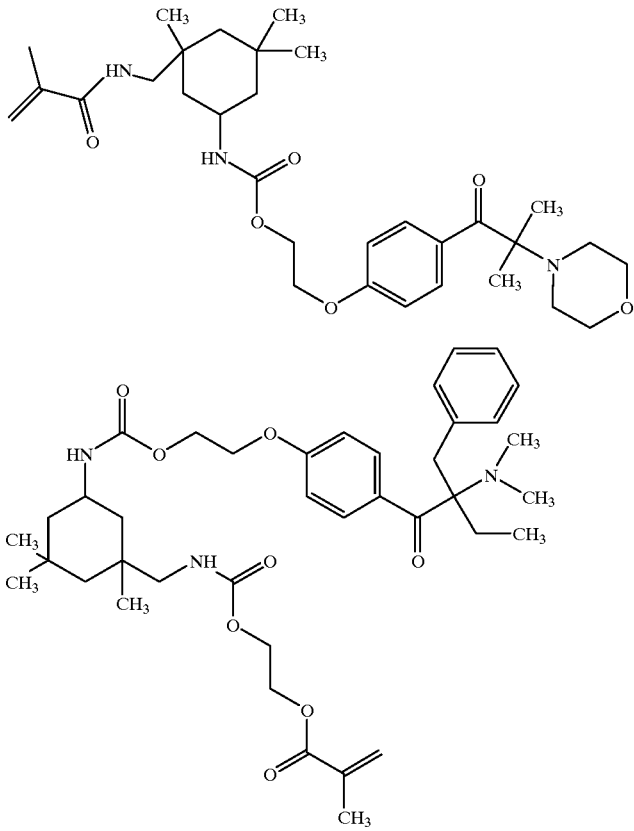

The compounds of formula (I) or (XVII) are outstandingly suitable as initiators for radiation-induced polymerisation of ethylenically unsaturated compounds. In the process, compounds according to formula (XVII) are incorporated into the polymers in their entirety or as fragments either via the unsaturated group and/or via the radicals formed. The oligomers and polymers according to the invention are also eminently suitable as initiators, it being possible to form graft polymers or also, depending upon the content of initiator groups in the macroinitiator, inter-penetrating and unconnected or only partially inter-connected polymer networks.

The invention further relates to dimeric photoinitiators of formula (XIX)

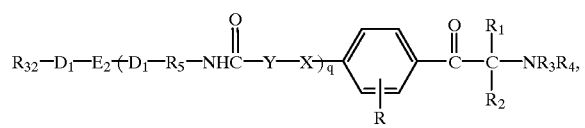
(XIX)

wherein $E_2$ is —$X_1$—$(CH_2)_m$—$X_1$— and each $X_1$ independently of the other is —O— or —NH— and m is an integer from 2 to 6, q is zero or 1, $D_1$ is —NHCO—, and $R_{32}$ is a radical of formula (XX)

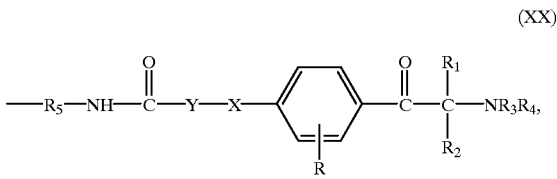
(XX)

wherein

X, Y, R, $R_1$, $R_2$, $R_3$, $R_4$ and $R_5$ have the definitions given hereinbefore, including the preferred definitions.

In a preferred embodiment, $X_1$ is either only —O— or only —NH—. In a highly preferred embodiment, $X_1$ is —O— and $D_1$ is —NHCO—, the carbonyl group of $D_1$ being linked to $E_2$. In a more highly preferred embodiment, $X_1$ is —O—, q is zero and $D_1$ is —NHCO—, the carbonyl group of $D_1$ being linked to $E_2$.

The invention further relates to trimeric photoinitiators of formula (XXI)

$$\{R_{33}\text{-}E_3\text{-}\}_3\text{-}T \qquad (XX),$$

wherein

R$_{33}$ is a compound of formula (XXI)

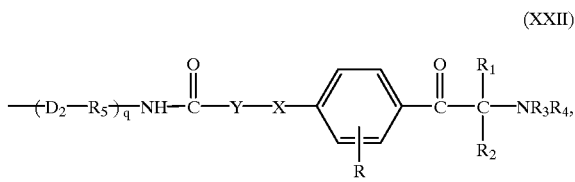

(XXII)

wherein
X, Y, R, R$_1$, R$_2$, R$_3$, R$_4$ and R$_5$ have the definitions given hereinbefore, including the preferred definitions,
q is independently of the other zero or 1,
D$_2$ is —NHCO—, —CONH— or —NHCONH—,
E$_3$ is lower alkylene and
T is a trivalent organic or inorganic radical.

In a preferred embodiment, E$_3$ is hexamethylene, each q is zero and T is a trivalent organic radical and, more preferably, is cyanuric acid less its 3 acidic hydrogen atoms.

Within the scope of the present invention, hereinbefore and hereinafter and unless stated otherwise, arylene is preferably phenylene or napthylene each unsubstituted or substituted by lower alkyl or lower alkoxy, especially 1,3-phenylene, 1,4-phenylene or methyl-1,4-phenylene, or 1,5-naphthylene or 1,8-naphthylene.

Within the scope of the present invention, aryl has up to 24, and preferably up to 18, carbon atoms and is a carbocyclic aromatic compound that is unsubstituted or substituted by lower alkyl or lower alkoxy. Examples are phenyl, toluyl, xylyl, methoxyphenyl, tert-butoxyphenyl, naphthyl or phenanthryl.

Within the scope of this invention, unless defined otherwise the term "lower" used in connection with radicals and compounds denotes especially radicals or compounds having up to 8 carbon atoms, preferably up to 6 carbon atoms.

Lower alkyl has especially up to 8 carbon atoms, preferably up to 6 carbon atoms, and is, for example, methyl, ethyl, propyl, butyl, tert-butyl, pentyl, hexyl or iso-hexyl.

Lower alkenyl is linear or branched alkenyl having from 2 to 8 carbon atoms, preferably from 2 to 6 carbon atoms and especially from 2 to 4 carbon atoms. Examples of alkenyl are vinyl, allyl, 1-propen-2-yl, 1-buten-2- or -3- or -4-yl, 2-buten-3-yl, and the isomers of pentenyl, hexenyl or octenyl.

Unless defined otherwise, alkylene has up to 10 carbon atoms and may be straight-chain or branched. Suitable examples include decylene, octylene, hexylene, pentylene, butylene, propylene, ethylene, methylene, 2-propylene, 2-butylene or 3-pentylene. Alkylene is preferably lower alkylene.

Lower alkylene is alkylene having up to 8, and especially up to 6, carbon atoms. An especially preferred definition of lower alkylene is methylene or ethylene.

The arylene unit of alkylenearylene or arylenealkylene is preferably phenylene that is unsubstituted or substituted by lower alkyl or lower alkoxy; the alkylene unit thereof is preferably lower alkylene, such as methylene or ethylene, especially methylene. Preferably, such radicals are therefore phenylenemethylene or methylenephenylene.

Lower alkoxy has especially up to 8 carbon atoms, preferably up to 6 carbon atoms, and is, for example, methoxy, ethoxy, propoxy, butoxy, tert-butoxy or hexyloxy.

Within the scope of the present invention, aryl-lower alkyl has up to 30, preferably up to 24, and especially up to 18, carbon atoms and is lower alkyl substituted by aryl. Examples of aryl-lower alkyl are benzyl, xylylmethyl, toluylethyl, phenylbutyl, tert-butoxyphenyl-methyl, naphthylpropyl, methoxyphenylmethyl or phenylhexyl.

The invention further relates to a radiation-sensitive composition comprising
a) at least one ethylenically unsaturated photo-polymerisable or photo-crosslinkable compound (hereinafter referred to as radiation-sensitive organic material) and
b) an effective initiator quantity of at least one compound of formula (I), (XVII), (XIX) or (XXI) or of an oligomer or polymer having structural units of formula (IV).

The compounds of component b) may be present in an amount of from 0.001 to 70% by weight, especially from 0.001 to 50% by weight, more especially from 0.01 to 40% by weight and most especially from 0.01 to 20% by weight, based on component a). The amount is mainly governed by the photoactive groups bonded in the initiator; the fewer that are present, the greater is the chosen amount to be added.

Ethylenically unsaturated photo-crosslinkable compounds and therewith also photo-structurisable materials are known. Such materials have been described, for example, by G. E. Green et al. in J. Macromol. Sci.; Revs. Macromol. and Chem., C21(2), 187–273 (1981 to 1982) and by G. A. Delzenne in Adv. Photochem., 11, pp. 1–103 (1979).

The radiation-sensitive organic material is preferably a monomeric, oligomeric or polymeric substance having photo-polymerisable ethylenically unsaturated groups, especially a non-volatile or not readily volatised substance of that kind.

Photo-polymerisable compounds are, for example, acrylic and especially methacrylic acid esters of alcohols and polyols, or acrylic and especially methacrylic acid amides of amines and polyamines, for example C$_1$–C$_{18}$alkanols, ethylene glycol, propanediol, butanediol, hexanediol, di(hydroxymethyl)cyclohexane, polyoxyalkylenediols, for example di-, tri- or tetra-ethylene glycol, di- or tri-1,2-propylene glycol, trimethylol-methane, -ethane or -propane and pentaerythritol, C$_1$–C$_{18}$alkylamines, ethylenediamine, diethylenetriamine and triethylenetetramine, which can be used alone, in mixtures or in admixture with binders. Also suitable are mono-, oligo- and poly-siloxanes having acrylic and especially methacrylic acid ester radicals that are bonded to pendant or terminal hydroxy(C$_2$–C$_{12}$alkyl) or amino(C$_2$–C$_{12}$alkyl) groups, for example 1-trimethylsilyl-3-methacroyloxypropane, 1-pentamethyldisiloxanyl-3-methacryloxypropane and 3-[tris(trimethylsiloxy)silyl]-propyl methacrylate. Also suitable are perfluoroalkyl acrylates and methacrylates.

The photo-polymerisable compounds may comprise other additives customary for processing or application, and, in addition, other conventional photoinitiators or photo-sensitizers.

The photo-polymerisation is carried out under the effect of radiation in the absence or presence of a solvent, preferably UV radiation, it being possible to use known radiation sources, for example mercury vapour lamps. If solvents are used, they are preferably inert solvents already mentioned by way of example above.

A compound according to formula (I) can also be bonded to surfaces of inorganic or organic materials (hereinafter referred to as substrates) that contain H-active —COOH, HO—, HS— or —NH— groups. Suitable methods for this are known, for example immersion, spraying, brushing, knife-coating, pouring, rolling and especially spin-coating or vacuum vapour deposition methods. A compound according to formula (I) is firmly anchored to the surface by reaction with the isocyanate group. This reaction may be carried out, for example, at elevated temperatures, for example from 0 to 100° C. and preferably at RT. After the reaction, excess compounds can be removed, for example, with solvents. There can then be applied to the modified surfaces photo-polymerisable compounds which are subsequently polymerised under the effect of radiation and firmly bound to the substrate by graft polymerisation by way of the photoinitiators. In the process, a tentacle-like or brush-like polymer structure is formed on the surface of the substrate, which is capable of substantially preventing the undesirable formation of irreversible deposits of, for example, proteins, lipids or salts in the biological medium (membrane fouling, lime deposits).

Suitable substrates are, for example, types of glass, silicate minerals (silica gels), metal oxides and, especially, natural or synthetic plastics which are known in great number.

Some examples of plastics are polyaddition and polycondensadon plastics (polyurethanes, epoxy resins, polyethers, polyesters, polyamides, polyimides); vinyl polymers (polyacrylates, polymethacrylates, polystyrene, polyethylene and its halogenated derivatives, polyvinyl alcohol (PVA), polyhydroxyethyl methacrylate, polyvinyl acetate and polyacrylonitrile); elastomers such as silicones, polybutadiene or polyisoprene, or polybutadiene cross-linked with a polysiloxane, optionally upon which a vinylic monomer is graft-polymerised; unmodified or modified bio-polymers (collagen, cellulose, chitosan and previously mentioned biopolymers). When substrates contain too few or no functional groups, it is possible to modify the surface of the substrates by methods known per se, for example plasma methods or oxidation or hydrolysis methods, and generate functional groups such as —OH, —NH$_2$ or —CO$_2$H.

The invention further relates to a material consisting of (a) an inorganic or preferably organic substrate to which (b) there is bonded as photoinitiator at least one compound of formula (I), which is firmly bound to the substrate by way of O atoms, S atoms, HN-C$_1$–C$_6$alkyl groups or NH groups, on the one hand, and by the isocyanate group of the photoinitiators, on the other hand, and, optionally, (c) a thin layer of a polymer on the photoinitiator layer, which polymer can be obtained by applying a thin layer of photo-polymerisable ethylenically unsaturated substances to the substrate surface provided with photoinitiator radicals and polymerisation of the layer of ethylenically unsaturated substances by irradiation, preferably with UV radiation.

The said material is preferably a biomedical material and, especially, an ophthalmic moulded article consisting of a transparent organic base material, for example a contact lens or an intraocular lens, especially a contact lens.

The layer thickness of the ethylenically unsaturated substances depends mainly upon the desired properties. It may be from 0.001 μm to 1000 μm, preferably from 0.01 μm to 500 μm, more preferably from 0.1 to 100 μm, especially from 0.5 to 50 μm and most especially from 1 to 20 μm. For the production of contact lenses specifically, a layer thickness of from 0.01 to 50 μm, preferably from 0.05 to 20 μm and especially from 0.1 to 5 μm is desirable. The layers can be produced by the coating methods mentioned hereinbefore.

The ethylenically unsaturated substances may be the compounds mentioned hereinbefore as photo-polymerisable compounds. Other suitable ethylenically unsaturated compounds are non-volatile substituted polyolefins, especially acrylic acid or methacrylic acid and their esters and amides, for example acrylic and methacrylic acid C$_1$–C$_{12}$alkyl esters or oligooxaalkylene esters or C$_1$–C$_{12}$hydroxyalkyl esters or amides (2,3-dihydroxypropyl methacrylate, NN-dimethylacrylamide, acrylamide, N,N-iethylaminoethyl methacrylate, oligoethylene oxide acrylates and methacrylates, 2-hydroxyethylmethacrylic acid esters, methyl methacrylate (MMA), polyethylene glycol 1000 that has been derivatised with from 1 to 2 molar equivalents of methacrylic acid (PEG(1000)MA), and N-vinylpyrrolidone.

The invention further relates to a process for modifying surfaces of inorganic or organic substrates that contain H-active HO-, HS-, HN-C$_1$–C$_6$alkyl groups or —NH$_2$— groups, comprising the steps of a) applying to the substrate a thin layer of a photoinitiator of at least one compound of formula (I), where appropriate together with a catalyst, for example dibutyltin dilaurate, b) where appropriate heating the coated material and washing off the excess photoinitiator, c) applying a thin layer of a photo-polymerisable ethylenically unsaturated substance to the substrate surface provided with said photoinitiator, and d) irradiating the layer containing the ethylenically unsaturated substance preferably with UV radiation.

Any non-covalently bonded polymers that may be formed can be removed after the polymerisation, for example by treatment with suitable solvents.

By the process according to the invention the surfaces can be modified in many ways and given particular properties for different uses. Depending upon the ethylenically unsaturated substances chosen it is possible to improve in a controlled manner, for example, mechanical properties, for example surface hardness, scratch-resistance, wettability, abrasion resistance, writability, colorability, adhesive strength of coatings and of coverings of various metal, ceramic or polymer materials, sliding properties, stability of liquid films, resistance to undesirable deposits and colonisation by microorganisms, and physical properties such as, for example, coefficient of friction, permeability to gases, liquids and dissolved inorganic or organic substances of low to high molecular weight, and transparency, an especially strong adhesion of the polymer layers being a special advantage.

The photoinitiators according to the invention and substrates modified by the photoinitiators are distinguished by a high chemical and photochemical reactivity. They may be used to form photoreactive materials that may be employed as coating materials, photo-structurisable materials, for composite materials and, especially, as materials for biomedical applications, for example contact lenses and surgical materials. The materials are especially suitable for the production of hydrophilic and biocompatible surfaces on contact lenses by graft polymerisation with the formation of a tentacle structure (brush structure) that is especially beneficial in terms of required properties.

Of particular importance are the high wettability and the maintenance of a stable film of moisture on the surface, for example a lachrymal fluid film on the surface of a contact lens. Also of great importance is the improvement of the behaviour in biological systems, for example an improved biocompatibility, protection against bio-erosion, prevention of plaque formation and of bio-fouling, and no blood clotting or toxic or allergic reactions.

The modified materials according to the invention are especially suitable for the production of contact lenses. With regard to contact lenses, the following improvements in properties are especially important: high wettability (small contact angle), high tear strength, good lubricating effect, high abrasion resistance, no or only negligible enzymatic degradation, no deposition of components from the lachrymal fluid (proteins, lipids, salts, cell degradation products), no affinity for cosmetics, volatile chemicals, such as solvents, dirt and dust, no attachment or nesting-in of microorganisms, and sliding properties for movement of the lens on the eye.

The materials modified in accordance with the invention are also suitable for the production of artificial blood vessels and other biomedical materials for prostheses, for surgery and for diagnostics, it being especially advantageous that endothelial cells can grow over these materials.

The invention further relates to a contact lens comprising (a) a transparent organic base material having functional groups, especially hydroxy, mercapto, amino, alkylamino or carboxy groups, and (b) a thin layer on the surface, consisting of constituents that are preferably derived from (b1) at least one photoinitiator of formula (I) and (b2) a graft polymer formed by photo-copolymerisation of an olefin.

The invention further relates to a contact lens comprising (a) a transparent organic base material having functional groups, especially hydroxy, mercapto, amino, alkylamino or carboxy groups, and (b) a thin layer on the surface, consisting of constituents that are preferably derived from at least one photoinitiator of formula (I) which is bonded to a functional group of the base material via an isocyanate group.

Suitable base materials (a) are, for example, unmodified or modified natural polymers, for example collagen, chitosan, hyaluronic acid and cellulose esters, such as cellulose acetate or cellulose butyrate. Suitable base materials are, for example, unmodified or modified synthetic polymers, for example polyvinyl alcohol, polyhydroxyethyl methacrylate, polyglyceryl methacrylate, and copolymers based on those polymers. Also suitable are natural and synthetic polymers, for example polymers having silicone, perfluoroalkyl and/or alkyl acrylate structural units, in which functional groups are generated on the surface by suitable methods, for example plasma treatment, etching or oxidation.

Suitable olefins of the above-mentioned graft polymer (b2) are, for example, acrylamide, N,N-dimethylacrylamide, methacrylamide, hydroxyethyl methacrylate, glyceryl methacrylate, oligoethylene oxide mono- and bis-acrylates, ethylene glycol dimethacrylate, methylene bisacrylamide, vinylcaprolactam, acrylic acid, methacrylic acid, fumaric acid monovinyl ester, vinyl trifluoroacetate and vinylene carbonate, it being possible for reactive esters to be subsequently hydrolysed if required.

In certain cases, it may be advantageous to use mixtures of two or more photoinitiators according to the invention. Mixtures with known photoinitiators can, of course, also be used, for example mixtures with benzophenone, acetophenone derivatives, bezoin ethers or benzil ketals.

To accelerate the photo-polymerisation arnines may be added, e.g. triethanolamine, N-methyl-diethanolamine, p-dimethylaminobenzoic acid ethyl ester or Michler's ketone. The action of the amines can be intensified by the addition of aromatic ketones of the benzophenone type.

The photo-polymerisation can also be accelerated by the addition of photo-sensitizers, which shift or broaden the spectral sensitivity. These are especially aromatic carbonyl compounds, for example derivatives of benzophenone, thioxanthone, anthraquinone and 3-acylcoumarin, and 3-(aroylmethylene)-thiazolines.

The effectiveness of the photoinitiators according to the invention can be increased by the addition of titanocene derivatives having fluoro-organic radicals, as are described in EP-A-122,223 and EP-A-186,626, for example in an amount of from 1 to 20%. Examples of such titanocenes are bis(methylcyclopentadienyl)-bis(2,3,6-trifluorophenyl)-titanium, bis(cyclopentadienyl)-bis(4-dibutylamino-2,3,5,6-tetrafluorophenyl)-titanium, bis(methyl-cyclopentadienyl)-2-(trifluoromethyl)phenyl-titanium isocyanate, bis(cyclopentadienyl)-2-(trifluoromethyl)phenyl-titanium trifluoroacetate or bis(methylcyclopentadienyl)-bis-(4-decyloxy-2,3,5,6-tetrafluorophenyl)-titanium. Liquid $\alpha$-aminoketones are especially suitable for these mixtures.

In addition to the photoinitiator, the photo-polymerisable mixtures may contain various additives. Examples of the latter are thermal inhibitors, which are intended to prevent premature polymerisation, such as, for example, hydroquinone or sterically hindered phenols. In order to increase the dark storage stability, it is possible to use, for example, copper compounds, phosphorus compounds, quaternary ammonium compounds or hydroxylamine derivatives. For the purpose of excluding atmospheric oxygen during the polymerisation paraffin or similar waxy substances may be added which migrate to the surface when polymerisation commences. As light-protecting agents it is possible to add, in small quantities, UV absorbers, for example those of the benzotriazole, benzophenone or oxalanilide type. Better still is the addition of light-protecting agents that do not absorb UV light, such as, for example, sterically hindered amines (HALS).

The photoinitiators according to the invention can be used for various other purposes. Their use in unpigmented, pigmented or coloured systems is also of importance, such as, for example, for printing inks, for photographic reproduction processes, image recording processes and for the manufacture of relief moulds.

Another important field of application comprises coating compositions, which may be pigmented or unpigmented. The mixtures are especially useful in white paints, by which $TiO_2$-pigmented coating compositions are understood. Other fields of application are radiation-curing of photoresists, the photo-crosslinking of silver-free films and the production of printing plates. Another use is for outdoor paints the surface of which subsequently cures in daylight.

The photoiniiators are advantageously used for the applications mentioned in amounts of from 0.1 to 20% by weight, preferably approximately from 0.5 to 5% by weight, based on the photo-polymerisable composition. The polymerisation is carried out in accordance with the known methods of photo-polymerisation by irradiation with light high in short-wave radiation. Suitable light sources are, for example, mercury medium-pressure, high-pressure and low-pressure radiators, super-actinic fluorescent tubes, metal halide lamps or lasers, the emission maxima of which lie in the range from 250 to 450 nm. In the case of a combination with photo-sensitizers or ferrocene derivatives, it is also possible to use longer-wavelength light or laser beams up to 600 nm.

According to the invention, the compounds of formula I, XVII, XIX or XXI or oligomers or polymers having structural units of formula IV can be used as photoinitiators for the photo-polymerisation of ethylenically unsaturated compounds and mixtures that comprise such compounds. The unsaturated compounds may contain one or more olefinic double bonds. They may be of low molecular weight (monomeric) or of higher molecular weight (oligomeric). Examples of monomers having one double bond are alkyl or hydroxyalkyl acrylates or methacylates, for example methyl, ethyl, butyl, 2-ethylhexyl or 2-hydroxy-ethyl acrylate, isobornyl acrylate, methyl or ethyl methacrylate. Other examples of these are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride or vinylidene chloride.

Examples of monomers having more than one double bond are ethylene glycol diacrylate, propylene glycol diacrylate, neopentyl glycol diacrylate, hexamethylene glycol diacrylate or bisphenol-A diacrylate, 4,4'-bis(2-acryloyloxyethoxy)diphenylpropane, trimethylol-propane triacrylate, pentaerydiritol tiiacrylate or tetraacrylate, vinyl acrylate, divinyl-benzene, divinyl succinate, diallyl phthalate, triallyl phosphate, triallyl isocyanurate or tris(2-acryloyloxyethyl) isocyanurate.

Examples of higher-molecular-weight (oligomeric) poly-unsaturated compounds are acrylated epoxy resins, acrylated polyethers, acrylated polyurethanes or acrylated polyesters. Other examples of unsaturated oligomers are unsaturated polyester resins, which are usually prepared from maleic acid, phthalic acid and one or more diols and have molecular weights of approximately from 500 to 3000. Such unsaturated oligomers can also be called pre-polymers.

Often used are two-component mixtures of a pre-polymer with a poly-unsaturated monomer or three-component mixtures that contain, in addition, a mono-unsaturated monomer. The pre-polymer is in this case primarily responsible for the properties of the coating film. By varying it, the person skilled in the art can influence the properties of the cured film. The poly-unsaturated monomer acts as a crosslinker which makes the coating film insoluble. The mono-unsaturated monomer acts as a reactive diluent by means of which the viscosity is reduced without the necessity to use a solvent.

Such two-component and three-component systems based on a pre-polymer are used both for printing inks and for surface coatings, photoresists or other photo-curable compositions. One-component systems based on photo-curable pre-polymers are also widely used as binders for printing inks.

Unsaturated polyester resins are mostly used in two-component systems together with a mono-unsaturated monomer, preferably with styrene. For photoresists, specific one-component systems are often used, for example polymaleimides, polychalkones or polyimides as described in DE-OS 2 308 830.

The unsaturated compounds can also be used in admixture with non-photo-polymerisable film-forming components. These may be, for example, physically drying polymers or solutions thereof in organic solvents, such as, for example, nitrocellulose or cellulose acetobutyrate. They may also, however, be chemically or thermally curable resins, such as, for example, polyisocyanates, polyepoxides or melamine resins. The concomitant use of thermally curable resins is important for the use in so-called hybrid systems which are photo-polymerised in a first step and crosslinked by thermal after-treatment in a second step.

The Examples given below serve to illustrate the present invention in more detail; they are not, however, intended to limit the scope thereof in any way. Unless stated otherwise, temperatures are given in degrees Celsius.

EXAMPLE A1

2-Dimethylamino-2-benzyl-1-(4-(2-hydroxyethoxy) phenyl)-butan-1-one.

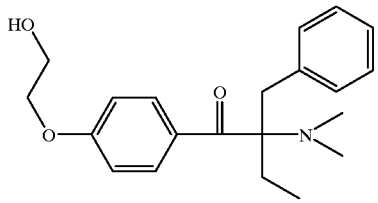

The title compound is prepared in accordance with the synthesis described in EP-A-284 561.

EXAMPLE A2

2-Ethyl-2-dimethylamino-1-(4-(2-hydroxyethoxy) phenyl)-pent-4-en-1-one.

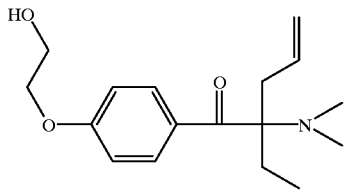

The title compound is prepared in quantitative yield analogously to Example A1. Yellowish crystals of m.p. 80–82° C. remain.

EXAMPLE A3

2-Ethyl-2-diethylamino-1-(4-(2-hydroxyethoxy)phenyl)-pentan-1-one.

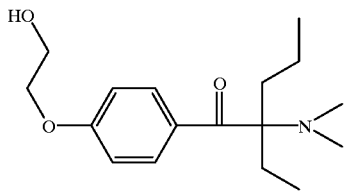

32.6 g (0.11 mol) of 2-ethyl-2-dimethylamino-1-(4-(2-hydroxyethoxy)phenyl)-pent-4-en-1-one according to Example A2 are dissolved in 220 ml of ethyl acetate, 1.6 g of palladium-on-carbon (5%) are added thereto and the mixture is then hydrogenated at 30° C. under normal pressure. After approximately 3 hours the absorption of hydrogen ceases (2.58 litres, 103% of the theoretical amount). The catalyst is removed by filtration and the solvent is distilled off using a rotary evaporator (RE). The oily residue is purified by flash-chromatography (petroleum ether/ethyl acetate 2:1). 27.4 g (84%) of a slightly yellowish oil remain.

EXAMPLE A4

1-(4-(2-Hydroxyethylthio)phenyl)-2-methyl-2-morpholino-propan-1-one.

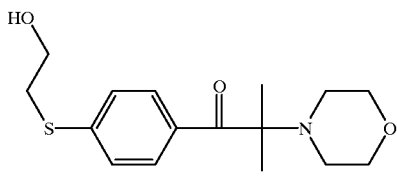

The preparation of the title compound is described in EP-A-088 050.

EXAMPLE A5

1-(4-(2-Hydroxyethoxy)phenyl)-2-methyl-2-morpholino-propan-1-one.

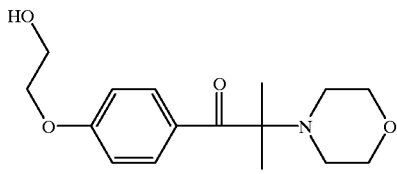

The title compound is prepared analogously to Example A4.

EXAMPLE A6

Preparation of a dimeric photoinitiator:

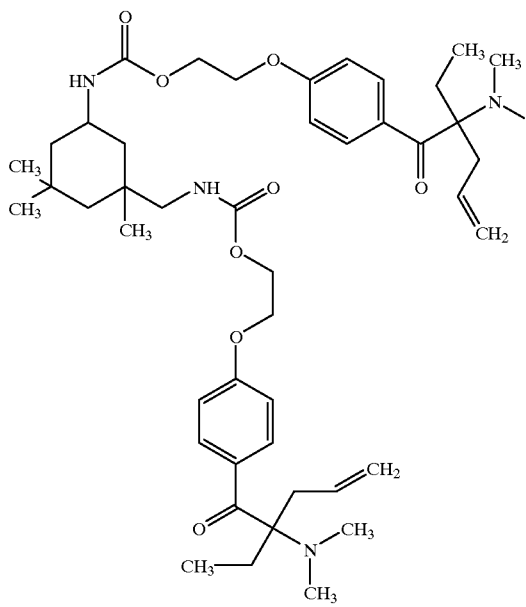

In a 250 ml flask equipped with reflux condenser, thermometer, stirrer and nitrogen inlet pipe, 5.8 g (20 mmol) of 2-ethyl-2-dimethylamino-1-(4-(2-hydroxyethoxy)phenyl)-pent-4en-1-one (from Example A2) and 2.2 g (10 mmol) of isophorone diisocyanate (IPDI) are dissolved in 100 ml of dry methylene chloride. 0.6 g (1 mmol) of the catalyst dibutyltin dilaurate (DBTDL) is added thereto and the batch is stirred at room temperature (RT) for 26 hours. The course of the reaction is monitored by thin-layer chromatography (TLC) (silica gel TLC plates, eluant petroleum ether/ethyl acetate 1:2). The reaction solution is then stirred into water, and the organic phase is separated off and washed twice more with water. The organic phase is dried over $MgSO_4$ and concentrated using a RE. The residue which remains is purified by flash-chromatography (petroleum ether/ethyl acetate 1:1). 6.3 g (78%) of a viscous yellow oil remain. Combustion analysis yields the following values:

| $C_{46}H_{68}O_8N_4$ (805.07) | calc. C 68.63 | H 8.51 | N 6.96% |
|---|---|---|---|
| | found C 68.31 | H 8.64 | N 6.98% |

EXAMPLES A7, A8, A9 and A10

Analogously to Example A6, the following dimeric photoinitiators are each prepared by reaction of 2 equivalents of a photoinitiator from Examples A1, A3, A4 and A5 and 1 equivalent of IPDI. All the structures are verified by proton NMR.

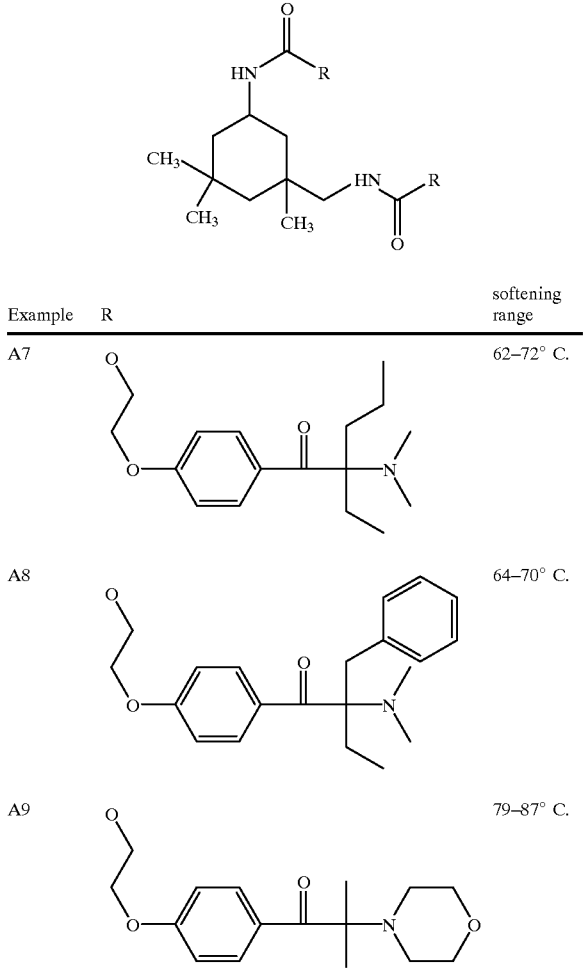

-continued

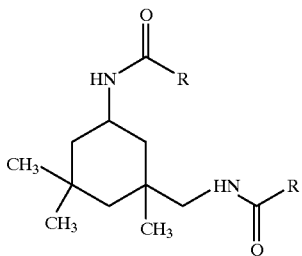

| Example | R | softening range |
|---------|---|----------------|
| A10 |  | 60–66° C. |

EXAMPLE A11

Preparation of:

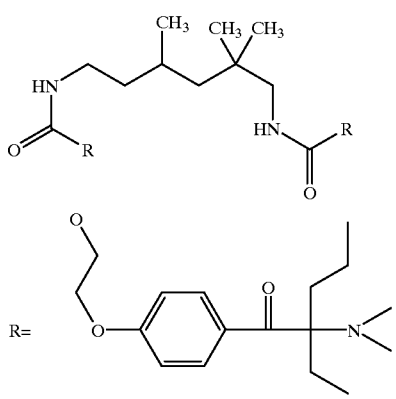

In a 250 ml flask equipped with reflux condenser, thermometer, stirrer and nitrogen inlet pipe, 8.8 g (30 mmol) of 2-ethyl-2-dimethylamino-1-(4-(2-hydroxyethoxy)phenyl)-pentan-1-one (from Example A3) and 3.15 g (15 mmol) of 2,2,4-trimethylhexamethylene diisocyanate (2,2,4-TMDI) are dissolved in 100 ml of dry methylene chloride. 0.95 g (1.5 mmol) of the catalyst DBTDL is added thereto and the batch is stirred under reflux for 14 hours. The course of the reaction is monitored by IR spectroscopy (IR band of the isocyanate group disappears at 2250 cm$^{-1}$). The reaction solution is then cooled to RT and stirred into water. The organic phase is separated off and washed twice more with water. The organic phase is dried over $MgSO_4$ and concentrated using a RE. The residue which remains is purified by flash-chromatography (petroleum ether/ethyl acetate 2:1). 7.3 g (61%) of a viscous oil remain. The structure is verified by proton NMR.

EXAMPLE A12

Analogously to Example A11, by reaction of 2 equivalents of the photoinitiator from Example A5 with 1 equivalent of diphenylmethane 4,4'-diisocyanate in methylene chloride and with the addition of 0.1 equivalent of DBTDL, the following compound is prepared:

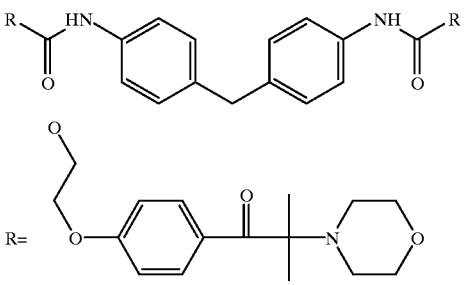

A beige powder having a softening range of 70–82° C. is obtained.

EXAMPLE A13

Analogously to Example A11, by reaction of 2 equivalents of the photoinitiator from Example A4 with 1 equivalent of hexamethylene diisocyanate in methylene chloride and with the addition of 0.1 equivalent of DBTDL, the following compound is prepared:

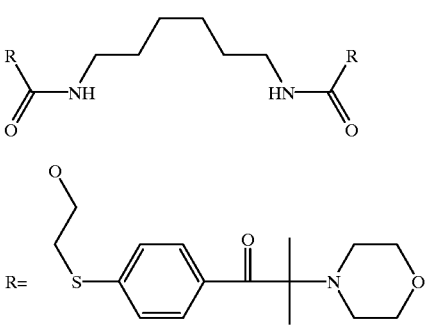

A yellowish resin is obtained in 98% yield.

EXAMPLE A14

Analogously to Example A11, by reaction of 2 equivalents of the photoinitiator from Example A5 with 1 equivalent of toluene 2,4-diisocyanate (TDI) in methylene chloride and with the addition of 0.1 equivalent of DBTDL, the following compound is prepared:

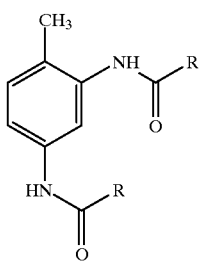

-continued

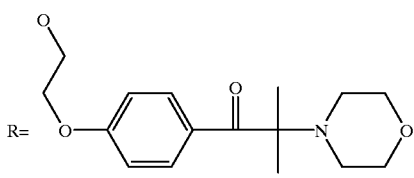

A beige powder having a softening range of 83–90° C. is obtained.

EXAMPLE A15

Analogously to Example A11, by reaction of 3 equivalents of the photoinitiator from Example A5 with 1 equivalent of Desmodur® 3390 in methylene chloride and with the addition of 0.1 equivalent of DBTDL, the following compound is prepared:

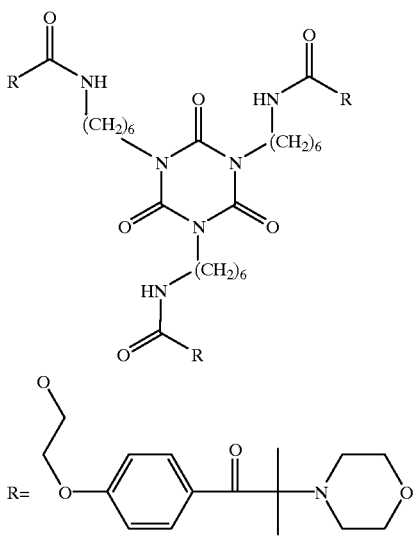

A beige powder having a softening range of 60–67° C. is obtained.

EXAMPLE A16

Analogously to Example A11, by reaction of 3 equivalents of the photoinitiator from Example A1 with 1 equivalent of Desmodur® 3390 in methylene chloride and with the addition of 0.1 equivalent of DBTDL, the following compound is prepared:

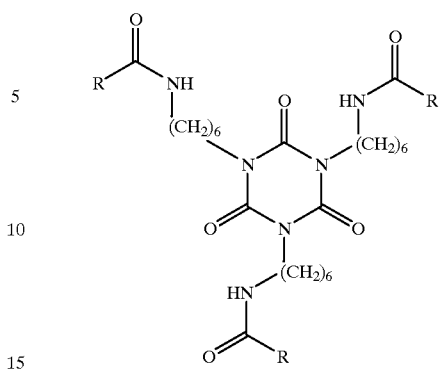

A yellowish resin is obtained.

EXAMPLE A17

Preparation of the following compound:

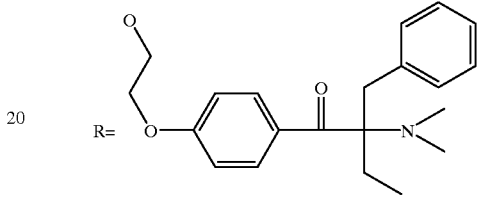

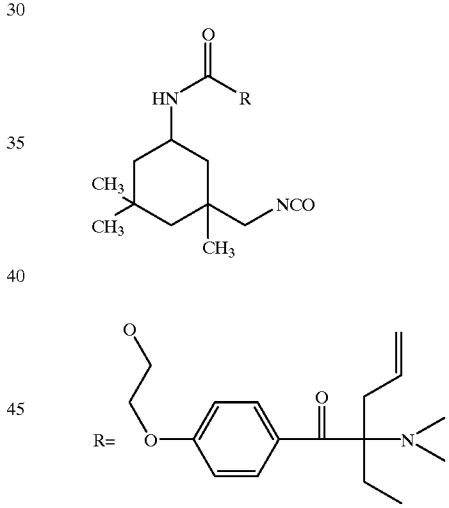

In a 100 ml flask equipped with reflux condenser, thermometer, stirrer and nitrogen inlet pipe, 2.92 g (10 mmol) of 2-ethyl-2-dimethylamino-1-(4-(2-hydroxyethoxy)phenyl)-pent-4-en-1-one (from Example A2) are dissolved in 30 ml of dry methylene chloride, and the solution is mixed with 2.22 g (10 mmol) of IPDI dissolved in 30 ml of dry methylene chloride. 2.0 mg of the catalyst DBTDL are added thereto and stirring is carried out at RT for 72 hours. The course of the reaction is monitored by TLC (eluant is toluene/acetone 6:1). The reaction solution is then stirred into water. The organic phase is separated off and washed twice more with water. The organic phase is dried over $MgSO_4$ and concentrated using a RE. The residue which remains is purified by column chromatography (toluene/acetone 6:1). 3.4 g (66%) of a yellow oil remain. The structure is verified by proton NMR, IR and elemental analysis.

EXAMPLE A18

Analogously to Example A17, the following isocyanate is prepared from 1.17 g (4 mmol) of 1-(4-(2-hydroxyethoxy)phenyl)-2-methyl-2-morpholino-propan-1-one (from Example A5) and 0.7 g (4 mmol) of 2,4-TDI using DBTDL as catalyst in methylene chloride. After the addition of 50 ml of ether and 200 ml of petroleum ether to the RM, the target compound precipitates in crystalline form. It is filtered off, washed with petroleum ether and then dried in vacuo to yield the compound below of m.p. 97–102° C.

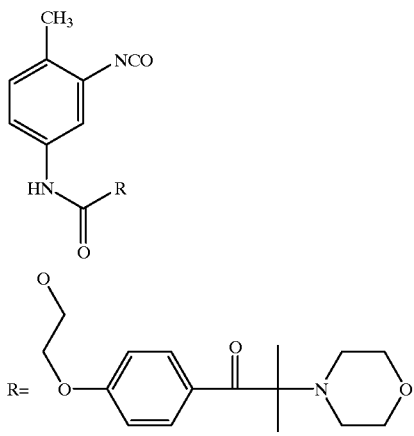

EXAMPLES A19, A20, and A21

Analogously to Example A17, the following compounds are prepared:

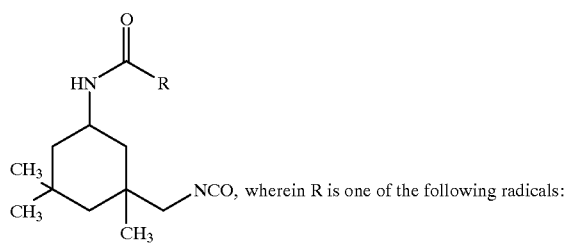

NCO, wherein R is one of the following radicals:

Example No. A19

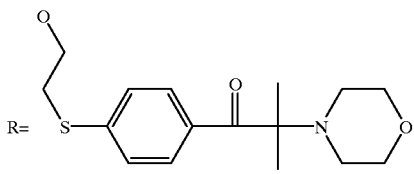

Example No. A20

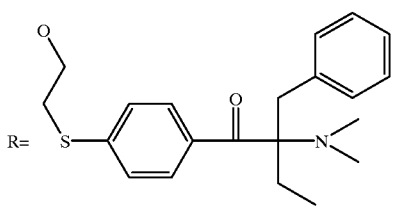

Example No. A21

EXAMPLE A22

Analogously to Example A17, the following compound is prepared:

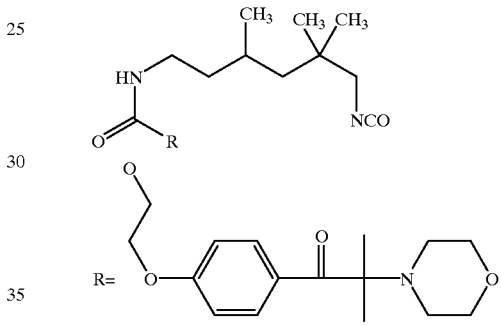

EXAMPLE A23

Analogously to Example A17, the following isocyanate is prepared from 5.1 g (29.3 mmol) of 2,4-toluene diisocyanate (TDI) and 10 g (29.3 mmol) of 2-dimethyl-amino-2-benzyl-1-(4-(2-hydroxyethoxy)phenyl)-butan-1-one (from Example A1) using DBTDL as catalyst in methylene chloride. The RM is diluted with 500 ml of diethyl ether and 2 litres of petroleum ether, whereupon the product precipitates. It is filtered off, washed with diethyl ether/petroleum ether and dried in vacuo. A beige powder having a softening range of 99–103° C. is obtained.

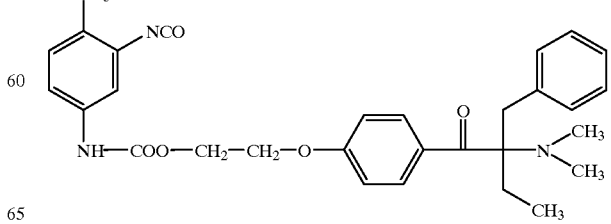

EXAMPLE B1

Preparation of an oligomeric photoinitiator:

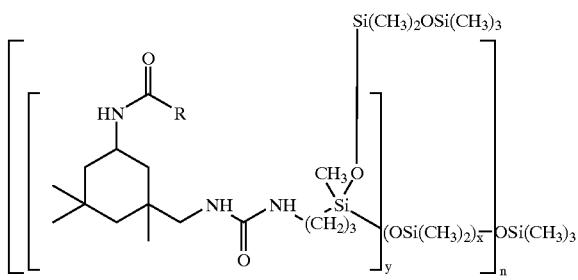

wherein R=

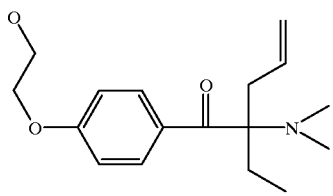

and x:y is approximately 27:1, and n is 5.

0.7 g (1.3 mmol) of the isocyanate from Example A17, 20 ml of dry methylene chloride and 2.55 g (0.51 mVal NH$_2$/g) of aminoalkylpolysiloxane KF 8003 (Shin Etsu, Japan) are placed in an apparatus according to Example A17. The reaction mixture is stred at RT for 2 hours and at 40° C. for 20 minutes. The solvent is then removed using a RE. The residue is freed of solvent residues under a high vacuum (40° C., 0.001 mbar (0.1 Pa)). The tile compound is obtained in quantitative yield. In the IR spectrum, there is no OCN band.

EXAMPLE B2

Analogously to Example B1, an oligomeric photoinitiator having the structure according to Example B1 is prepared from 0.76 g (1.3 mmol) of isocyanate from Example A21 and 2.55 g (0.51 mVal NH$_2$/g) of aminoalkylpolysiloxane KF 8003 (Shin Etsu, Japan), wherein R has the following definition:

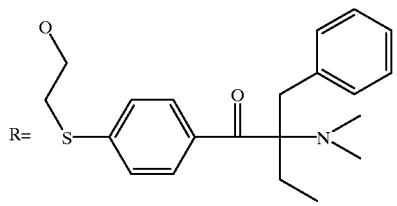

EXAMPLE B3

Analogously to Example B1, an oligomeric photoinitiator having the following structure is prepared from 0.55 g (0.97 mmol) of isocyanate from Example A20 and 1.47 g (0.7 mVal NH$_2$/g) of aminoalkylpolysiloxane X-22-161B (Shin Etsu, Japan):

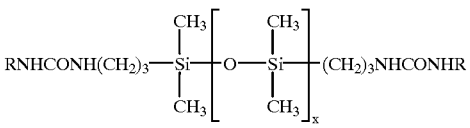

wherein x is approximately 38, and R corresponds to the radical of the title compound of Example A20 less the isocyanate.

EXAMPLE B4

Analogously to Example B1, a solution of 1.0 g (1.95 mmol) of the isocyanate from Example A17 in 20 ml of dry acetonitrile is mixed with 2.24 g (0.84 mVal NH$_2$/g) of Jeffamin ED 2001 (Texaco, USA) in 30 ml of dry acetonitrile and the mixture is stirred at RT for 24 hours. After working-up, 3.2 g (99%) of the following photoinitiator are obtained:

R—NHCONH—CHCH$_3$CH$_2$—(OCHCH$_3$CH$_2$)$_a$—(OCH$_2$CH$_2$)$_b$—(OCHCH$_3$CH$_2$)$_c$—NHCONH—R wherein a+c=2.5 and b=40.5, and R corresponds to the radical of the title compound of Example A17 less the isocyanate.

EXAMPLE B5

In an apparatus according to Example A17, 1.65 g of polyvinyl alcohol (PVA) (Serva® 03/20, molecular weight approximately 13000) are dissolved at 80° C. under nitrogen in dry NMP. The solution is then cooled to RT and a solution of 1.0 g (1.88 mmol) of the isocyanate from Example A19 in 10 ml of dry NMP, and 5 mg of DBTDL as catalyst are added thereto. This mixture is then heated at 40° C. for 48 hours. After that time, no OCN is detectable by IR at 2250 cm$^{-1}$. The RM is cooled to RT and 700 ml of diethyl ether are added thereto, the product precipitating. After filtration, washing with diethyl ether and then drying under a high vacuum, 1.9 g of a white product remain which, according to elemental analysis, comprises 2.20% S. Proton NMR is consistent with the following structure:

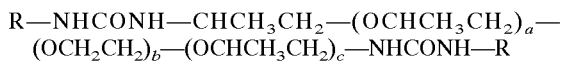

wherein n is approximately 10 and a:b=20:1; and R corresponds to the radical of the title compound of Example A19 less the isocyanate.

EXAMPLES B6, B7 and B8

Analogously to Example B5, two hydroxyalkyl-substituted polydimethylsiloxanes (KF-6002/KF-6001) and one dextran are reacted with the isocyanate from Example A19. The following parameters describe those compounds. The yields are approximately 90% in all cases. The sulfur content of those compounds is determined by combustion analysis (last column of the Table).

| isocyanate from Example A19 | OH-macromer | solvent | S-content (%) calc./found |
|---|---|---|---|
| 0.5 g (0.94 mmol) | KF-6002, Shin-Etsu, JP 1.5 g (0.63 Val OH/g) | THF | 1.50/1.38 |
| 0.5 g | KF-6001, Shin-Etsu, JP | | 2.22/2.08 |

-continued

| isocyanate from Example A19 | OH-macromer | solvent | S-content (%) calc./found |
|---|---|---|---|
| (0.94 mmol) 0.5 g (0.94 mmol) | 0.85 g (1.1 mVal OH/g) Dextran 8, Serva G 2.3 g, MW ≈ 8 – 12 000 | THF DMSO | 1.08/0.99 |

EXAMPLE B9

Analogously to Example B5, 3.23 g of collagen (Serva 17440, MW≈80000) are dissolved in DMSO over the course of 12 hours and then 1.0 g (1.9 mmol) of isocyanate from Example A20 in 10 ml of DMSO is added. After stirring the reaction mixture at RT for 72 hours, it is diluted with 500 ml of methanol, whereupon the product precipitates. The product is filtered off and washed repeatedly with dry THF. It is then dried under a high vacuum (0.1 Pa, RT, 72 hours). 2.8 g of a yellow-white product remain, the IR spectrum and proton NMR of which are consistent with the expected structure.

The Production of Polymer Films and Contact Lenses

EXAMPLE C1

5 g of poly(1,2-syndiotactic)-butadiene (PB) from Polysciences Inc. (Catalogue No. 16317, MW≈10000) are dissolved at 40° C. in 100 ml of THF. The solution is then cooled to RT and poured onto a Folanorm sheet (Folex®, Zürich, Switzerland) to produce a film of a PB solution of approximately 0.5 mm thickness. The THF is slowly evaporated at RT under nitrogen. The polybutadiene film which remains is then extracted with ethanol and dried until its weight is constant.

EXAMPLE C2

2.2 g of PB are dissolved in 50 ml of methylcyclohexane at 40° C. under nitrogen. A solution of 2 g of H-siloxane (Experimental Product K-3272, Goldschmidt, Germany) in 5 ml of methylcyclohexane is added thereto and stirng is carried out for 5 minutes. This solution is then gassed with nitrogen for 30 minutes. There are then added to this solution 3 drops of the catalyst platinum divinyltetramethyldisiloxane (ABCR, PC 072) dissolved in 1 ml of methylcyclohexane and the mixture is then heated at 50° C., with stirring, for 3 minutes. This mixture is then placed between two glass plates to produce a liquid film of approximately 1.5 mm thickness. This sandwich system is then heated at 60° C. under nitrogen for 16 hours. It is then cooled to RT, the glass plates are removed and the crosslinked polybutadiene film is extracted with THF. After extraction, the crosslinked polybutadiene film is dried until its weight is constant.

EXAMPLE C3

5.35 g (1 mmol) of vinyl-containing polysiloxane (Silopren U Additiv V 200, Bayer Leverkusen, Germany) are mixed with 1.13 g (2 mmol) of H-siloxane (Experimental Product 1085, Goldschmidt, Germany) and the mixture is stirred at RT under reduced pressure (200 mbar (20 kPa)) for one hour. Nitrogen is then bubbled through the mixture for 30 minutes, 2 drops of the catalyst platinum divinyltetramethyldisiloxane (ABCR, PC 072) are added and the mixture is stirred for 5 minutes. Polypropylene (PP) moulds (Ciba Vision Atlanta, for moulded articles of 0.5 mm thickness) are then filled with this mixture, closed and heated in an oven at 60° C. under nitrogen for 16 hours. The moulds are allowed to cool to RT and are opened, and the disks so produced, which contain cross-linked polyvinylsiloxane, are extracted with ethanol and subsequently dried until their weight is constant.

EXAMPLE C4

Contact lenses consisting of crosslinked polyvinyl siloxane are produced analogously to Example C3, using polypropylene moulds suitable for the production of soft contact lenses having a thickness of 100 μm, a diameter of 1.4 cm and a base curve of 8.4 mm.

EXAMPLE C5

2.63 g (0.5 mmol) of vinyl-containing polysiloxane (Silopren U Additiv V 200) and 3.0 g of H-siloxane (Experimental Product K 3272, Goldschmidt, Germany) are mixed and stirred at RT under reduced pressure (200 mbar (20 kPa)) for one hour. Nitrogen is then bubbled through the mixture for 30 minutes, 2 drops of the catalyst platinum divinyltetra-methyldisiloxane (ABCR, PC 072) are added and the mixture is stirred for 10 minutes. Polypropylene contact lens moulds (Ciba Vision Atlanta, USA) are then filled with this mixture, closed and heated in an oven at 60° C. under nitrogen for 16 hours. The moulds are allowed to cool to RT and are opened, and the contact lenses so produced, which contain crosslinked polyvinylsiloxane, are extracted with ethanol and subsequently dried until their weight is constant.

EXAMPLE D1

4 g of photoinitiator from Example A17 are dissolved under nitrogen in 10 ml of acetone. A portion of this solution is sprayed onto a polybutadiene film according to Example C1, so that, after the acetone has been evaporated while flushing with nitrogen, an even photoinitiator film is produced on the polybutadiene film. The coated polybutadiene film is then irradiated with UV light (12 mW/cm$^2$) for 10 minutes. The film is subsequently washed three times with acetone in order to remove non-bonded photoinitiator. The film is then dried under reduced pressure (0.001 bar (0.1 Pa)) until its weight is constanl The Fourier-transform IR spectrum (FT-IR) of the film exhibits an OCN band at 2250 cm$^{-1}$. Finally, the film is immersed for 2 hours in a 5% Jeffamin M 2070 solution in acetone and is then thoroughly washed twice with acetone and three times with deionised water. The polybutadiene film so coated is analysed in FT-IR and then the contact angles are determined (K 12, Krüss GmbH, Hamburg, Germany).

| polybutadiene film C1 | contact angle in [°] | |
|---|---|---|
| | advancing | receding |
| uncoated | 102 | 78 |
| coated | 66 | 47 |

EXAMPLE D2

Analogously to Example D1, a crosslinked polybutadiene film from Example C2 is coated.

| polybutadiene film C2 | contact angle in [°] | |
|---|---|---|
| | advancing | receding |
| uncoated | 111 | 71 |
| coated | 96 | 59 |

EXAMPLE D3

Analogously to Example D1, a polybutadiene film from Example C1 is coated with the photoinitiator from Example A19.

| polybutadiene film C1 | contact angle in [°] | |
|---|---|---|
| | advancing | receding |
| uncoated | 102 | 78 |
| coated | 62 | 46 |

EXAMPLE D4

Analogously to Example D1, contact lenses from Example C4 are coated with the photoinitiator from Example A19.

| polyvinylsiloxane C4 | contact angle in [°] | |
|---|---|---|
| | advancing | receding |
| uncoated | 111 | 78 |
| coated | 98 | 34 |

EXAMPLE D5

Analogously to Example D1, a crosslinked polyvinylsiloxane disk from Example C3 is coated with the photoinitiator from Example A17.

| disk from C3 | contact angle in [°] | |
|---|---|---|
| | advancing | receding |
| uncoated | 112 | 72 |
| coated | 99 | 38 |

EXAMPLE D6

Analogously to Example D1, a polybutadiene film according to Example C1 is coated with the photoinitiator from Example A17. In contrast to Example D1, however, this film is then immersed in a DMSO solution comprising 1% Dextran 8 (Serva) and approximately 1 mg of DBTDL as catalyst.

| polybutadiene film C1 | contact angle in [°] | |
|---|---|---|
| | advancing | receding |
| uncoated | 102 | 78 |
| coated | 98 | 51 |

EXAMPLE D7

Analogously to Example D1, a polybutadiene film according to Example C1 is coated with the photoinitiator from Example A17. In contrast to Example D1, however, this film is then immersed in an aqueous solution comprising 5% polyethyleneimine (Fluka).

| polybutadiene film C1 | contact angle in [°] | |
|---|---|---|
| | advancing | receding |
| uncoated | 102 | 78 |
| coated | 66 | 18 |

EXAMPLE D8

Analogously to Example D1, contact lenses according to Example C5 are coated with the photoinitiator from Example A17. In constrast to Example D1, however, these lenses are then immersed in an aqueous solution comprising 5% polyethyleneimine (Fluka).

| contact lenses from C5 | contact angle in [°] | |
|---|---|---|
| | advancing | receding |
| uncoated | 115 | 80 |
| coated | 99 | 56 |

EXAMPLE E1

2 g of the macrophotoinitiator according to Example B5 are dissolved in 50 ml of dry DMSO. Nitrogen is bubbled through this solution for 30 minutes. A polybutadiene film from Example C1 (2×2 cm) is then immersed in this solution for 10 minutes, then removed and irradiated with UV light (12 mW/cm$^2$) for 10 minutes. The film so coated is washed once with DMSO, twice with isopropanol, once with 50% aqueous isopropanol and once with water. The film is then dried and analysed (layer thickness of the hydrophilic film is approximately 6 μm, determined by means of optical microscopy and RuO$_4$ contrasting.

| polybutadiene film C1 | contact angle in [°] | |
|---|---|---|
| | advancing | receding |
| uncoated | 102 | 78 |
| coated | 48 | 37 |

EXAMPLE E2

Analogously to Example E1, a crosslinked polybutadiene film from Example C2 is treated with the macrophotoinitiator from Example B5.

| polybutadiene film C2 | contact angle in [°] | |
| --- | --- | --- |
| | advancing | receding |
| uncoated | 111 | 71 |
| coated | 97 | 38 |

EXAMPLE E3

Analogously to Example E1, siloxane disks from Example C3 are treated with the macrophotoinitiator from Example B8.

| siloxane disks from C3 | contact angle in [°] | |
| --- | --- | --- |
| | advancing | receding |
| uncoated | 112 | 72 |
| coated | 94 | 36 |

EXAMPLE E4

Analogously to Example E1, contact lenses from Example C4 are treated with the macrophotoinitiator from Example B5.

| contact lenses from C4 | contact angle in [°] | |
| --- | --- | --- |
| | advancing | receding |
| uncoated | 111 | 78 |
| coated | 88 | 37 |

EXAMPLE E5

Analogously to Example E1, contact lenses from Example C5 are treated with the macrophotoinitiator from Example B8.

| contact lenses from C5 | contact angle in [°] | |
| --- | --- | --- |
| | advancing | receding |
| uncoated | 115 | 70 |
| coated | 76 | 41 |

EXAMPLE F1

Polyvinylsiloxane contact lenses according to Example C3 are placed in a plasma reactor. The reactor chamber is then charged with argon for 1 minute under glow discharge conditions and then with 1,2-diaminocyclohexane under the following conditions: radio frequency of 27.12 MHz, 30 Watt output, 0.3 mbar (30 Pa) pressure, flow rate of operating gas 3.65 cm³/min (STP), residence time of the lenses in the reactor is 5 minutes. The reactor is then flushed with nitrogen and the lenses are removed.

EXAMPLE F2

The contact lenses treated according to Example F1 are immersed for 30 minutes at room temperature (RT) and under nitrogen in an acetonitrile solution comprising 1% by weight of the photoinitiator from Example A17. The reactive photoinitiator is thereby bonded to the amino groups generated on the surface of the lenses by the plasma treatment. The contact lenses are subsequently washed with acetonitrile for 12 hours and then dried in vacuo for 3 hours.

EXAMPLE F3

1.5 g (20 mmol) of acrylamide are dissolved in 10 ml of distilled water in a round-bottomed flask with stirring at RT and gassing with nitrogen. This solution is then de-gassed under reduced pressure and then gassed with nitrogen again for 30 minutes. The solution is then filtered (pore size 0.45 µm) and a sufficient quantity is poured into a petri dish for contact lenses from Example F2, placed in that solution, to be covered by about 1 mm of the solution. Irradiation (12 mW/cm²) is then carried out from both sides for 3 minutes using a mercury high-pressure lamp (2000 Watt). The lenses are then removed from the bath and washed repeatedly with water. Extraction is then carried out for a further 24 hours with HPLC-water. The lenses are dried in vacuo and then analysed by FT-IR, AFM and contact angle measurement.

EXAMPLES F4, F5, F6 and F7

Contact lenses from Example F2 comprising a covalently bonded photoinitiator are modified analogously to Example F3 using, in place of acrylamide (AA), aqueous solutions of other monomers. The contact angles of those contact lenses before and after such a coating are reproduced in the following Table.

| | | contact angle in [°] | | | |
| --- | --- | --- | --- | --- | --- |
| Ex- | | untreated | | treated | |
| ample | monomer | advancing | receding | advancing | receding |
| F3 | AA | 111 | 78 | 42 | 22 |
| F4 | NVP | 111 | 78 | 54 | 23 |
| F5 | HEMA | 111 | 78 | 72 | 32 |
| F6 | PEG(1000)MA | 111 | 78 | 61 | 11 |
| F7 | DMA | 111 | 78 | 36 | 18 |

AA=acrylamide, NVP=N-vinyl-2-pyrrolidone, HEMA= hydroxyethyl methacrylate, PEG(1000)MA=methacrylic acid that has been derivatised once or twice with polyethylene glycol 1000, DMA=N,N-dimethylacrylamide.

EXAMPLE G1

0.3 g of macrophotoinitiator from Example B1 is dissolved under nitrogen in 0.4 g of dry THF. To the solution are added 0.2 g of freshly distilled NVP and 0.1 g of ethylene glycol dimethacrylate (EGDMA) and stirling is carried out for 15 minutes. Gassing with nitrogen is then carried out for 30 minutes. The solution is then filtered (pore size 0.45 µm)

into a bottle. Under nitrogen, clean PP moulds are filled with this solution (180 to 200 μl per mould), and the moulds are closed and irradiated with UV light (12 mW/cm²) for 15 minutes. The moulds are opened and the mould halves, containing the lenses, are placed in an ethanol bath, whereupon the lenses separate from the mould halves. The lenses are then extracted in ethanol for a further 24 hours and are subsequendy dried in vacuo.

EXAMPLE G2

Analogously to Example G1, lenses are produced from 40 g of macrophotoinitiator from Example B1, 15 g of DMA, 5 g of EGDMA and 40 g of THF.

EXAMPLE G3

Analogously to Example G1, lenses are produced from 34.5 g of macrophotoinitiator from Example B1, 59.5 g of 3-[tris(trimethylsiloxy)silyl]-propyl methacrylate (TRIS) and 6 g of NVP, the TRIS and NVP acting as solvents for the photoinitiator. The radiation time for this mixture is 20 minutes.

EXAMPLE G4

Analogously to Example G3, lenses are produced from 57 g of macrophotoinitiator from Example B1, 37 g of 3-[tris(trimethylsiloxy)silyl]-propyl methacrylate (TRIS) and 3 g of NVP and 3 g of EGDMA.

The following Table gives information on the properties of the contact lenses so produced.

| Example | water absorption(%) | stress (MPa) tensile strength | strain(%) elongation at break | E-modulus (MPa) |
| --- | --- | --- | --- | --- |
| G1 | 47.5 | 1 | 37 | 8.8 |
| G2 | 39.1 | 1 | 69 | 3.6 |
| G3 | 5.2 | 1 | 974 | 0.1 |
| G4 | 2.5 | 3 | 89 | 10.5 |

EXAMPLE G5

0.16 g of macrophotoinitiator from Example B5 are dissolved under nitrogen in 0.82 g of a solution of N-methylpyrrolidone (NMP) in DMSO (70:12). 20 μg of the crosslinker EGDMA are added and gassing with nitrogen is carried out for 20 minutes. The solution is then filtered (Teflon filter of pore size 0.45 μm) into a bottle. Under nitrogen, clean PP moulds are filled with this solution (180 to 200 μl per mould), and the moulds are closed and irradiated with UV light (12 mW/cm²) for 30 minutes. The moulds are opened and the mould halves, containing the lenses, are placed in an ethanol bath, whereupon the transparent, slightly yellow lenses separate from the mould halves. The lenses are then extracted in ethanol for a further 24 hours and are subsequently dried in vacuo.

EXAMPLE G6

Analogously to Example G5, contact lenses are produced from 0.1 g of macrophotoinitiator from Example B5, 0.5 g of DMSO, 0.4 g of NVP and 20 μg of EGDMA.

EXAMPLE G7

0.25 g of macrophotoinitiator from Example B8 are dissolved under nitrogen in 0.5 g of dry DMSO. 0.25 g of HEMA and 20 μg of the crosslinker EGDMA are added and gassing with nitrogen is subsequently carried out for 30 minutes. The solution is then filtered (pore size 0.45 μm) and introduced under nitrogen into clean PP moulds. Irradiation and working-up are carried out as described in Example G5.

| Example | water absorption(%) | stress (MPa) tensile strength | strain(%) elongation at break | E-modulus (MPa) |
| --- | --- | --- | --- | --- |
| G5 | 178 | 0 | 496 | 0.04 |
| G6 | 441 | 0 | 73 | 0.24 |
| G7 | 18.8 | 0 | 67 | 0.52 |

EXAMPLE G8

2.0 g of macroinitiator from Example B3 are dissolved under nitrogen in 3 g of dry THF. 2 g of this solution are mixed with 0.9 g of freshly distilled NVP and gassing with nitrogen is carried out for 30 minutes. Under nitrogen, clean PP moulds are then filled with this solution (approximately 200 μl of solution per mould), closed and irradiated with UV light (12 mW/cm²) for 10 minutes. The moulds containing the highly viscous polymer solution are then freed of THF in a drying cupboard at 40° C. Clear, slightly yellow disks that are soluble in ethanol remain.

EXAMPLE G9

Analogously to Example G8, transparent, slightly opaque disks are produced from a mixture of 2.0 g of macroinitiator from Example B3 and 0.9 g of DMA.

EXAMPLE H1

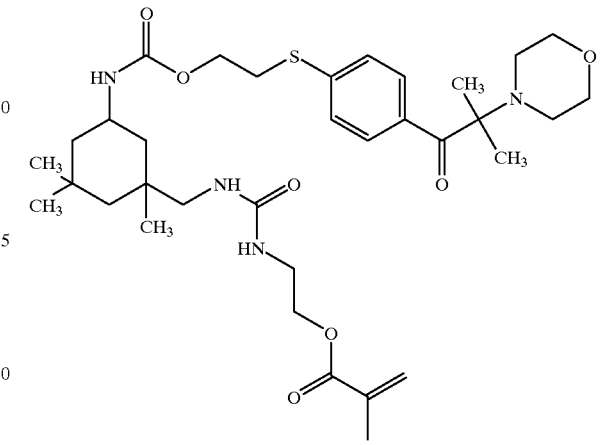

In a sulfonating flask, 0.31 g (1.88 mmol) of 2-aminoethyl methacrylate hydrochloride are introduced into 10 ml of dry acetonitrile with stirring. There are then added dropwise under nitrogen, simultaneously but from different dropping funnels, 1.0 g (1.88 mmol) of reactive photoinitiator from Example A19 dissolved in 10 ml of dry acetonitrile and 190 mg (1.88 mmol) of triethylamine dissolved in 5 ml of dry acetonitrile. Stiring is carried out at RT for a further 72 hours. The course of the reaction is monitored during that time with TLC. The reaction mixture is then poured onto 100 ml of water, the mixture is stirred and then extraction is carried out 3 times with toluene. The organic phase is separated off, dried and concentrated using a RE. The residue is purified by chromatography on silica gel (toluene/acetone 8:2). The IR spectrum, the proton NMR and elemental analysis are consistent with the structure.

| microanalysis | C % | H % | N % | S % |
|---|---|---|---|---|
| calc. | 61.79 | 7.93 | 8.48 | 4.85 |
| found | 62.20 | 7.92 | 7.69 | 4.99 |

EXAMPLE H2

In an apparatus analogous to Example H1, 0.46 g (3.5 mmol) of HEMA are introduced into 10 ml of acetone and there are then added at RT under nitrogen, with stirring, 1.97 g (3.5 mmol) of photoinitiator from Example A20 dissolved in 10 ml of acetone. To this are added 10 μg of dibutyl-p-cresol as inhibitor and 10 μg of DBTDL as catalyst. The reaction mixture is then stirred at 40° C. under nitrogen for 24 hours. During that time, the isocyanate group disappears from the IR spectrum. The RM is concentrated using a RE and the residue is purified by chromatography on silica gel.

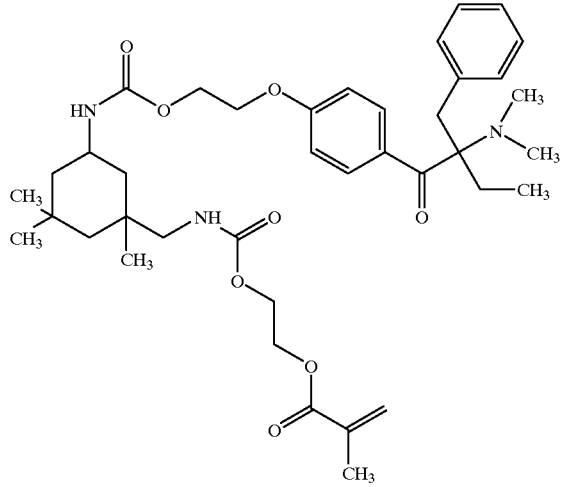

EXAMPLE H3

In an apparatus analogous to Example H1, 0.5 g (0.97 mmol) of photoinitiator from Example A23 are introduced into 5 ml of methylene chloride. There are then added at RT under nitrogen, with stirring, 0.13 g (0.97 mmol) of HEMA dissolved in 3 ml of methylene chloride. After the addition of 10 μg of dibutyl-p-cresol as inhibitor and 10 gg of DBTDL as catalyst, the solution is stirred at RT for a further 48 hours. The isocyanate group disappears during that time (IR monitoring). The RM is concentrated using a RE and the residue is purified by chromatography on silica gel (toluene/acetone 8:2).

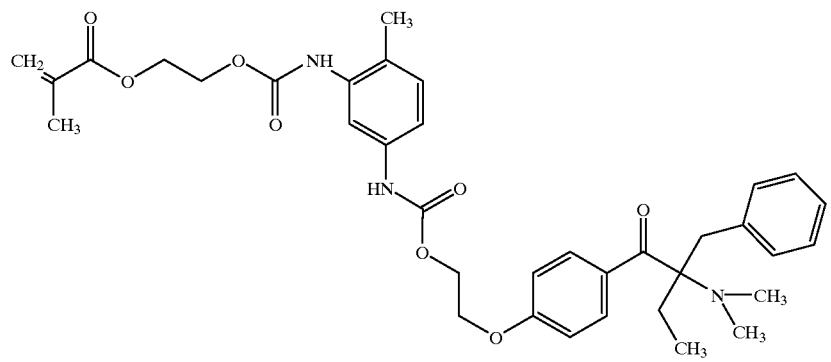

EXAMPLE H4

In a brown round-bottomed flask equipped with reflux condenser, thermometer, stirrer and argon inlet pipe, 2.0 g (3.0 mmol) of the compound from Example H1 are dissolved in 12 ml of toluene and then mixed with 6 g (60 mmol) of MMA. 0.2 g of the initiator azoisobutyronitrile (AIBN) is added thereto. This solution is heated at 60° C. for 20 hours. It is then cooled to RT, diluted with 20 ml of toluene, and 2000 ml of diethyl ether are added thereto, whereupon a solid precipitates. The solid is filtered off, washed with a small amount of diethyl ether and dried in vacuo. A white powder remains, the proton NMR of which is consistent with the following structure, the ratio of a:b being 1:20.

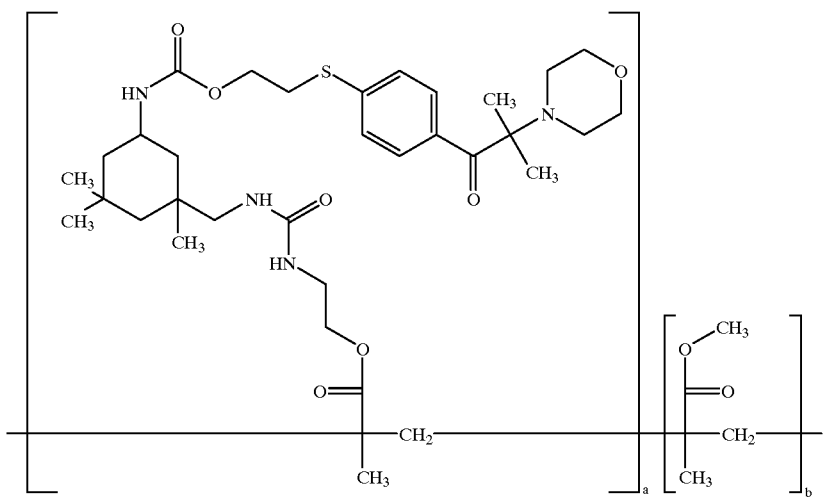

EXAMPLE H5

Analogously to Example H4, a copolymer is prepared from 0.65 g (1 mmol) of the polymerisable photoinitiator from Example H3, 1 g (10 mmol) of MMA and 1.0 g of TRIS.

EXAMPLE H6

320 mg of macroinitiator from Example H4 are dissolved under nitrogen in 1.4 ml of dry THF. To the solution there are added 85 mg of freshly distilled NVP and 30 mg of EGDMA and stirring is carried out for 15 minutes. Gassing with nitrogen is then carried out for 30 minutes. This solution is filtered (filter of 0.45 µm pore size). Clean PP moulds are filled under nitrogen with the filtered solution (approximately 200 µl of solution per mould). The moulds are closed and irradiated with UV light (12 mW/cm$^2$) for 10 minutes. The moulds are opened, and the mould halves, containing the lenses, are placed in a THF bath, whereupon the lenses separate from the mould halves. After extraction with THF, the clear, transparent lenses are dried and analysed. The water absorption is 8.1%.

EXAMPLE I1

The photo-curing of a blue printing ink will be described. First, a blue printing ink is prepared according to the following recipe:

62.5 parts Setalin®565 (urethane acrylic resin from Synthese, Holland), 15 parts 4,4'-di(β-acryloyloxyethoxy)diphenylpropane-2,2 (Ebecryl®150, UCB, Belgium)

22.5 parts Irgalithblau®GLSM (CIBA-GEIGY AG, Basle).

The mixture is homogenised and milled to a particle size of <5 µm in a three-roll mill. 5 g portions of this printing ink are each homogeneously mixed with the desired amount of photoinitiator on a disk rubbing machine under a pressure of 180 kg/m$^2$ with water cooling. Samples comprising 3% photoinitiator (based on the printing ink) are prepared. Offset prints of those printing inks are made with a sample printing machine (from Prüfbau, FRG) on 4×20 cm strips of art paper. The printing conditions are:

printing ink coverage: 1.5 g/cm$^2$ pressing pressure (linear pressure): 25 kp/cm printing speed: 1 m/sec A print roller having a metal surface (aluminium) is used for this. The printed samples are cured in a UV irradiation device produced by PPG, using a lamp and an energy of 80 W/cm. The irradiation time is varied by varying the transport speed of the sample. Surface drying of the printing ink is tested immediately after irradiation by the so-called transfer test. In that test, a white paper is pressed against the printed sample under a linear pressure of 25 kp/cm. If the paper remains ink-free, the test has been passed. If visible amounts of ink are transferred to the test strip, this is an indication that the surface of the sample has not yet cured sufficiently. The following Table gives the maximum transport speed at which the transfer test was still passed. To test the full curing of the printing ink, offset prints are also made as described above, except that print rollers having a rubber surface are used and the metal side of aluminium-coated paper strips is printed The irradiation is carried out as described above. Immediately after the irradiation, the full curing is tested in a REL full cure testing device. In that test, an aluminium cylinder covered with cloth is placed on the printed sample and rotated once about its own axis within 10 seconds under a pressure of 1220 g/cm$^2$. If visible damage occurs on the sample, the printing ink has not full-cured sufficiendy. The following Table gives the maximum transport speed at which the REL test is still passed.

| Photoinitiator Example No. | Transfer Test (m/min) | REL Test (m/min) |
|---|---|---|
| A6 | 80 | 30 |
| A7 | 70 | 40 |
| A9 | 70 | 40 |
| A11 | 70 | 40 |
| A14 | 70 | 30 |
| A15 | 30 | 30 |

EXAMPLE I2

Reactivity of a resist formulation. A photo-curable formulation is prepared by mixing the following components:

10 g dipentaeiythritol monohydroxypentaacrylate (SR 399, Sartomer Co., Berkshire GB)

15 g tripropylene glycol diacrylate (Sartomer Co., Berkshire GB)

15 g N-vinylpyrrolidone, Fluka 10 g trismethylpropane triacrylate, Degussa 50 g urethane acrylate Actylan AJ 20, Société National des Poudres et Explosifs 0.3 g levelling auxiliary Byk 300, Byk-Mallinckoodt.

Portions of this composition are mixed with 2% (based on the solids content) of a photoinitiator (according to the following Table). These samples are applied to a 300 μm thick aluminium foil. The thickness of the dry layer is 60 μm. To that film there is applied a 76 μm thick polyester film onto which is laid a standardised test negative having 21 steps of differing optical density (Stouffer step wedge). The sample is covered with a second UV-taansparent sheet and pressed by vacuum onto a metal plate. Exposure is carried out for 20 seconds at a distance of 30 cm by means of a 5 kW MO 61 metal halide lamp. After the exposure, the sheet and mask are removed and the exposed layer is developed in ethanol for 10 seconds at 23° C. in an ultrasound bath. Drying is carried out at 40° C. for 5 minutes in a circulating air oven. The sensitivity of the initiator system used is characterised by giving the last wedge step imaged without stickiness. The higher is the step number, the more sensitive is the tested system.

In a second test series, the procedure described above is followed, except that, in addition to the 2% of a photoinitiator (according to the Example mentioned), 0.2% of isopropyl-thioxanthone (Quantacure ITX, International Bio-Synthetics) is added as sensitizer to the photo-curable mixture.

The results of the two test series are summarised in the following Table. It will be seen that the reactivity of the photoinitiators can be increased by the addition of a small amount of the Quantacure ITX sensitizer.

| Photoinitiator Example No. | Quantacur ITX | highest step imaged |
|---|---|---|
| A11 | — | 14 |
| A11 | 0.2% | 16 |
| A16 | — | 14 |
| A16 | 0.2% | 15 |
| A8 | — | 14 |
| A8 | 0.2% | 15 |

What is claimed is:

1. A contact lens comprising an oligomer or polymer having H-active groups —OH and/or —NH— bonded to the oligomer or polymer backbone, optionally via a bridge group, or having H-active —NH— groups bonded in the oligomer or polymer backbone, the H atoms of which H-active groups are partly or completely substituted by a radical of formula IV

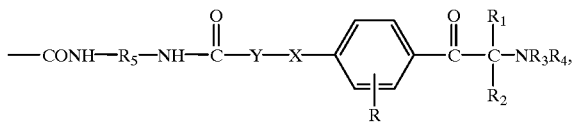

(IV)

wherein X is bivalent —O—, —NH—, —S—, alkylene having up to 8 carbon atoms or

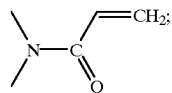

Y is a direct bond or —O—$(CH_2)_n$— wherein n is an integer from 1 to 6 and the terminal $CH_2$ group of which is linked to the adjacent X in formula (I);

R is H, $C_1$–$C_{12}$ alkyl, $C_1$–$C_{12}$ alkoxy, $C_1$–$C_{12}$ alkylNH- or —$NR_{1A}R_{1B}$ wherein $R_{1A}$ is alkyl having up to 8 carbon atoms and $R_{1B}$ is H or alkyl having up to 8 carbon atoms;

$R_1$ is linear or branched alkyl having up to 8 carbon atoms, alkenyl having from 2 to 8 carbon atoms or aryl-alkyl having up to 8 carbon atoms in the alkyl moiety;

$R_2$ independently of $R_1$ has the same definitions as $R_1$ or is aryl, or $R_1$ and $R_2$ together are —$(CH_2)_m$— wherein m is an integer from 2 to 6;

$R_3$ and $R_4$ are each independently of the other linear orbranched alkyl having up to 8 carbon atoms that may be substituted by $C_1$–$C_4$ alkoxy, or aryl-alkyl having up to 8 carbon atoms in the alkyl moiety or alkenyl having from 2 to 8 carbon atoms; or $R_3$ and $R_4$ together are —$(CH_2)_z$—$Y$—$(CH_2)_z$— wherein the two valences are each attached to the N-atom, $Y_1$ is a direct bond, —O—, —S— or —$NR_{1B}$—, and $R_{1B}$ is H or alkyl having up to 8 carbon atoms and z is independently of the other an integer from 2 to 4; and $R_5$ is branched $C_3$–$C_{18}$alkylene, unsubstituted or $C_1$–$C_4$alkyl- or $C_1$–$C_4$ alkoxy-substituted $C_6$–$C_{10}$ arylene, or unsubstituted or $C_1$–$C_4$ alkyl- or $C_1$–$C_4$ alkoxy-substituted $C_7$–$C_{18}$ aralkylene, unsubstituted or $C_1$–$C_4$alkyl- or $C_1$–$C_4$ alkoxy-substituted $C_{13}$–$C_{24}$-arylenealkylenearylene, unsubstituted or $C_1$–$C_4$ alkyl- or $C_1$–$C_4$alkoxy-substituted $C_3$–$C_8$-cycloalkylene, unsubstituted or $C_1$–$C_4$ alkyl- or $C_1$–$C_4$ alkoxy-substituted $C_3$–$C_8$cycloalkylene-$C_yH_{2y}$— or unsubstituted or $C_1$–$C_4$ alkyl- or $C_1$–$C_4$ alkoxy-substituted —$C_yH_{2y}$—($C_3$–$C_8$-cycloalkylene)-$C_yH_{2y}$—, wherein y is an integer from 1 to 6.

2. A contact lens according to claim 1, comprising a thin outer layer on at least a portion of the surface, consisting of a graft polymer formed by photo-polymerisation of an olefin.

3. A process for modifying surfaces of a contact lens or ophthalmic moulded article that contain H-active HO-, HS-, HN-$C_1$–$C_6$alkyl groups or —$NH_2$— groups, comprising the steps of a) applying to the substrate a thin layer of a photoinitiator of at least one compound of formula (I):

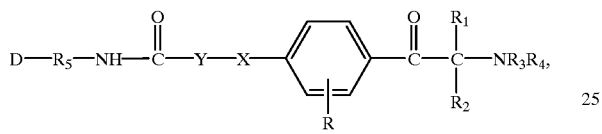

(I)

wherein X is bivalent —O—, —NH—, —S—, alkylene having up to 8 carbon atoms, or

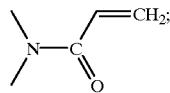

Y is a direct bond or —O—$(CH_2)_n$— wherein n is an integer from 1 to 6 and the terminal $CH_2$ group of which is linked to the admacent X in formula (I);

R is H, $C_1$–$C_{12}$alkyl, $C_1$–$C_{12}$alkoxy, $C_1$–$C_{12}$ alkylNH- or —$NR_{1A}R_{1B}$ wherein $R_{1A}$ is alkyl having up to 8 carbon atoms and $R_{1B}$ is H or alkyl having up to 8 carbon atoms;

$R_1$ is linear or branched alkyl having up to 8 carbon atoms, alkenyl having from 2 to 8 carbon atoms or aryl-alkyl having up to 8 carbon atoms in the alkyl moiety;

$R_2$ independently of $R_1$ has the same definitions as $R_1$ or is aryl, or $R_1$ and $R_2$ together are —$(CH_2)_m$— wherein m is an integer from 2 to 6;

$R_3$ and $R_4$ are each independently of the other linear or branched alkyl having up to 8 carbon atoms that may be substtuted by $C_1$–$C_4$ alkoxy, or aryl-alkyl having up to 8 carbon atoms in the alkyl moiety or alkenyl having from 2 to 8 carbon atoms; or $R_3$ and $R_4$ together are —$(CH_2)_z$—$Y_1$—$(CH_2)_z$— wherein the two valences are each attached to the N-atom, $Y_1$ is a direct bond, —O—, —S— or —$NR_{1B}$—, and $R_{1B}$ is H or alkyl having up to 8 carbon atoms and z is independently of the other an integer from 2 to 4;

$R_5$ is branched $C_3$–$C_{18}$ alkylene, unsubstituted or $C_1$–$C_4$ alkyl- or $C_1$–$C_4$ alkoxy-substituted $C_6$–$C_{10}$arylene, or unsubstituted or $C_1$–$C_4$alkyl- or $C_1$–$C_4$ alkoxy-substituted $C_7$–$C_{18}$ aralkylene, unsubstituted or $C_1$–$C_4$ alkyl- or $C_1$–$C_4$ alkoxy-substituted $C_{13}$–$C_{24}$arylene-alkylenearylene, unsubstituted or $C_1$–$C_4$ alkyl- or $C_1$–$C_4$ alkoxy-substituted $C_3$–$C_8$cycloalkylene, unsubstituted or $C_1$–$C_4$alkyl- or $C_1$–$C_4$ alkoxy-substituted $C_3$–$C_8$cycloalkylene-$C_yH_{2y}$— or unsubstituted or $C_1$–$C_4$ alkyl- or $C_1$–$C_4$ alkoxy-substituted —$C_yH_{2y}$—($C_3$–$C_8$cycloalkylene)- $C_yH_{2y}$—, wherein y is an integer from 1 to 6; and D is an isocyanato group;

b) heating the coated material and washing off the excess photoinitiator, c) applying a thin layer of a photo-polymerisable ethylenically unsaturated substance to the substrate surface provided with said photoinitiator, and d) irradiating the layer containing the ethylenically unsaturated substance optionally with UV radiation.

4. A contact lens or moulded ophthalmic article produced by the process of claim 3.

* * * * *